US 8,528,463 B2

(12) United States Patent
Hallberg et al.

(10) Patent No.: US 8,528,463 B2
(45) Date of Patent: *Sep. 10, 2013

(54) MODULAR SYSTEM FOR ORGANOSOLV FRACTIONATION OF LIGNOCELLULOSIC FEEDSTOCK

(75) Inventors: Christer Hallberg, Vancouver (CA); Donald O'Connor, Delta (CA); Michael Rushton, West Vancouver (CA); Edward Kendall Pye, Burnaby (CA); Gordon Gjennestad, Burnaby (CA); Alex Berlin, Burnaby (CA); John Ross MacLachlan, Burnaby (CA)

(73) Assignee: Lignol Innovations Ltd., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/555,664

(22) Filed: Jul. 23, 2012

(65) Prior Publication Data

US 2012/0289685 A1    Nov. 15, 2012

Related U.S. Application Data

(60) Division of application No. 12/268,417, filed on Nov. 10, 2008, now Pat. No. 8,227,004, which is a continuation of application No. 12/022,831, filed on Jan. 30, 2008, now Pat. No. 7,465,791, which is a continuation of application No. 12/016,932, filed on Jan. 18, 2008, now abandoned, which is a continuation-in-part of application No. 11/839,378, filed on Aug. 15, 2007, now abandoned.

(60) Provisional application No. 60/941,220, filed on May 31, 2007.

(51) Int. Cl.
*B01J 19/00*    (2006.01)

(52) U.S. Cl.
USPC ............... 99/275; 99/276; 99/277; 426/481; 530/500; 422/187; 435/294.1; 435/161

(58) Field of Classification Search
USPC ...... 426/481; 530/500; 422/187; 435/294.1, 435/161
See application file for complete search history.

(56) References Cited

U.S. PATENT DOCUMENTS 5,730,837 A    3/1998    Black et al.
(Continued)

FOREIGN PATENT DOCUMENTS

CA    1201115    2/1986
CA    1230592    12/1987
(Continued)

OTHER PUBLICATIONS

New Zealand Office Action date Oct. 29, 2010 received on corresponding New Zealand patent application No. 580751.
(Continued)

*Primary Examiner* — Anthony Weier
(74) *Attorney, Agent, or Firm* — Gowling Lafleur Henderson LLP

(57) ABSTRACT

A modular process for organosolv fractionation of lignocellulosic feedstocks into component parts and further processing of said component parts into at least fuel-grade ethanol and four classes of lignin derivatives. The modular process includes a first processing module configured for physicochemically digesting lignocellulosic feedstocks with an organic solvent thereby producing a cellulosic solids fraction and a liquid fraction, a second processing module configured for producing at least a fuel-grade ethanol and a first class of novel lignin derivatives from the cellulosic solids fraction, a third processing module configured for separating a second class and a third class of lignin derivatives from the liquid fraction and further processing the liquid fraction to produce a distillate and a stillage, a fourth processing module configured for separating a fourth class of lignin derivatives from the stillage and further processing the stillage to produce a sugar syrup.

19 Claims, 9 Drawing Sheets

(56) References Cited

U.S. PATENT DOCUMENTS

| | | | |
|---|---|---|---|
| 5,788,812 A | 8/1998 | Agar et al. | |
| 5,879,463 A | 3/1999 | Proenca | |
| 5,916,780 A | 6/1999 | Foody et al. | |
| 7,465,791 B1* | 12/2008 | Hallberg et al. | 530/500 |
| 8,067,193 B2 | 11/2011 | Hughes et al. | |
| 8,193,324 B2* | 6/2012 | Hallberg et al. | 530/500 |
| 8,227,004 B2* | 7/2012 | Hallberg et al. | 426/481 |
| 2008/0295980 A1* | 12/2008 | Hallberg et al. | 162/14 |
| 2012/0237980 A1* | 9/2012 | Hallberg et al. | 435/72 |

FOREIGN PATENT DOCUMENTS

| | | |
|---|---|---|
| CA | 2419658 | 3/2002 |
| WO | 2008/008793 A2 | 1/2008 |

OTHER PUBLICATIONS

Chinese Office Action date Feb. 24, 2011 received on corresponding Chinese patent application No. 2011022100348110.

\* cited by examiner

Fig. 7
(a)
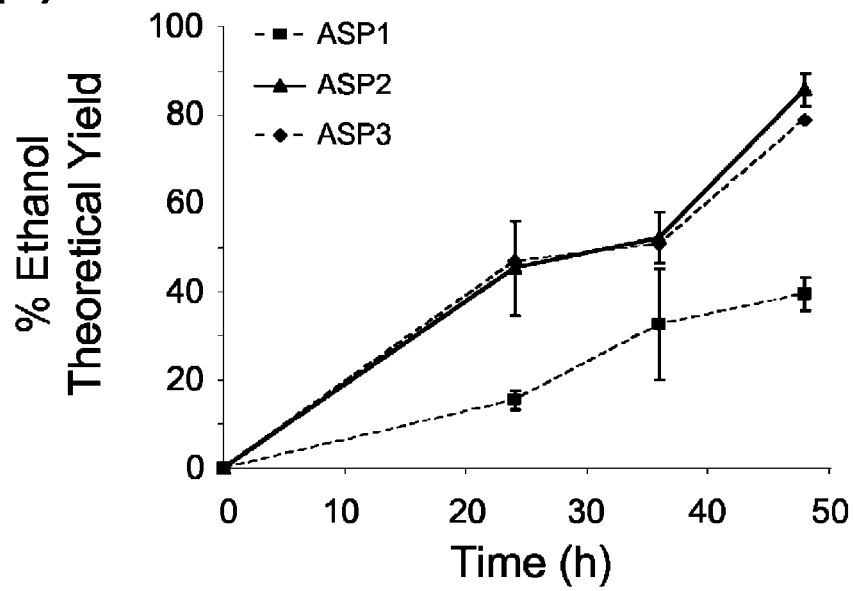
(b)
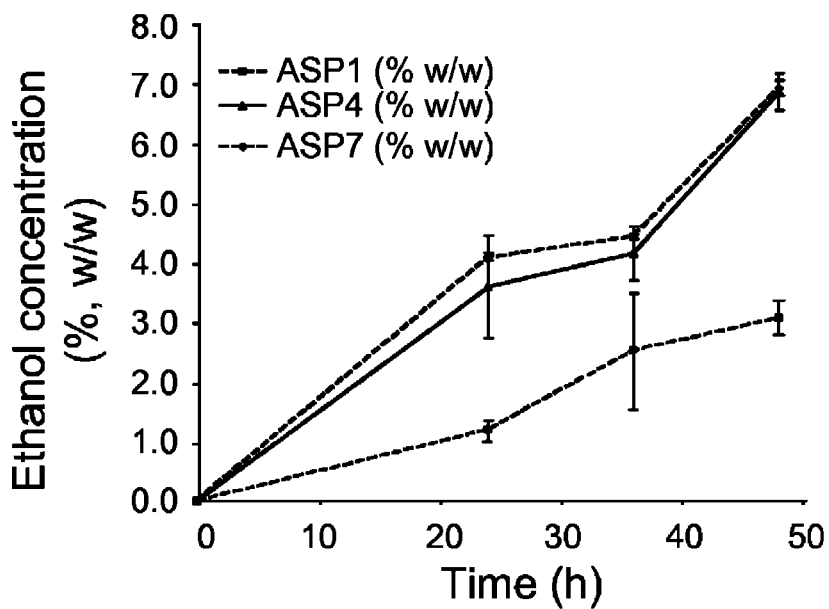

Fig. 8
(a)
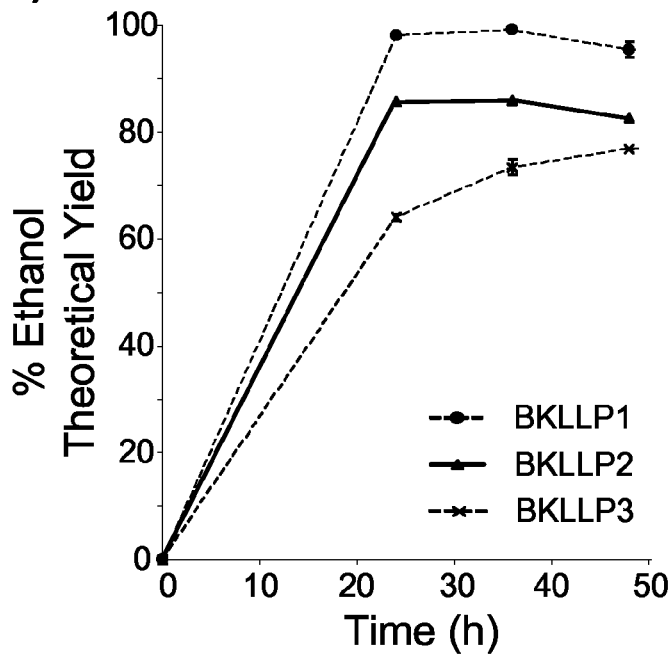
(b)
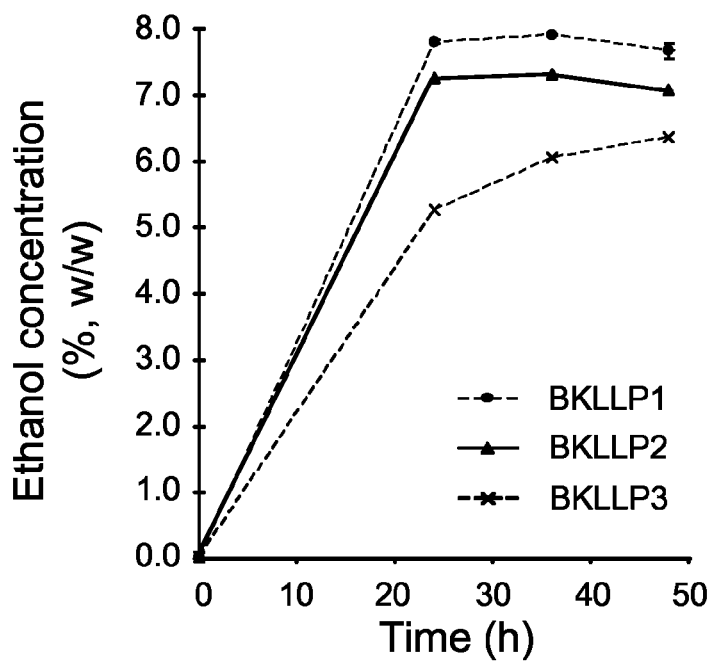

Fig. 9
(a)
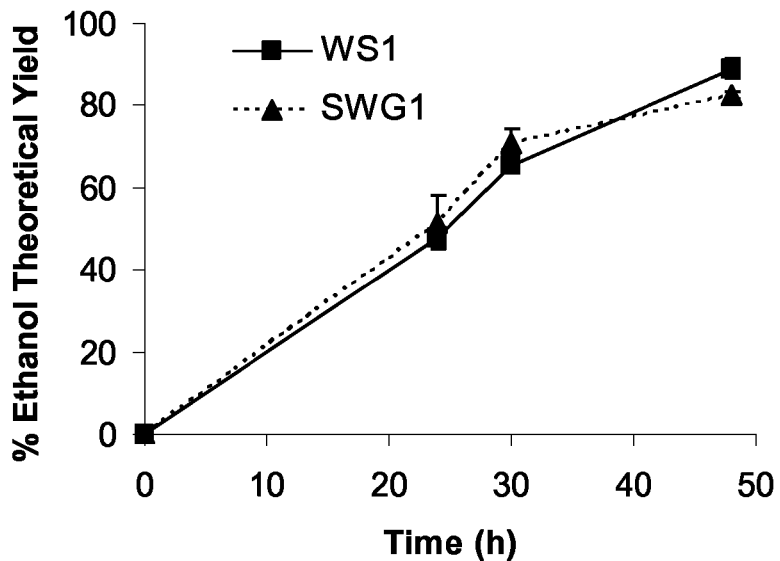
(b)
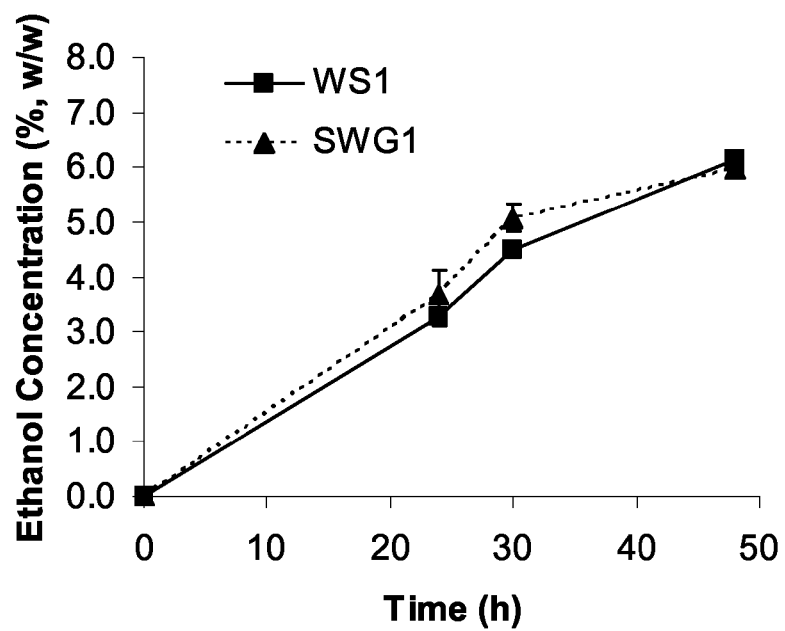

MODULAR SYSTEM FOR ORGANOSOLV FRACTIONATION OF LIGNOCELLULOSIC FEEDSTOCK

CROSS-REFERENCE TO RELATED APPLICATIONS

This application is a divisional application of U.S. patent application Ser. No. 12/268,417 filed Nov. 10, 2008 now U.S. Pat. No. 8,227,004, which is a Continuation of application Ser. No. 12/022,831 filed on Jan. 30, 2008, now U.S. Pat. No. 7,465,791, which is a Continuation of application Ser. No. 12/016,932 filed on Jan. 18, 2008 now abandoned, which is a Continuation-in-part of application Ser. No. 11/839,378 filed Aug. 15, 2007 now abandoned, and claims the benefit of U.S. Provisional Application No. 60/941,220 filed May 31, 2007.

FIELD OF THE INVENTION

This invention relates to fractionation of lignocellulosic feedstocks into component parts. More particularly, this invention relates to processes, systems and equipment configurations for recyclable organosolv fractionation of lignocellulosic material for continuous controllable and manipulable production and further processing of lignins, monosaccharides, oligosaccharides, polysaccharides and other products derived therefrom.

BACKGROUND OF THE INVENTION

Industrial processes for production of cellulose-rich pulps from harvested wood are well-known and typically involve the steps of physical disruption of wood into smaller pieces and particles followed by chemical digestion under elevated temperatures and pressures to dissolve and separate the lignins from the constituent cellulosic fibrous biomass. After digestion has been completed, the solids comprising the cellulosic fibrous pulps are separated from the spent digestion liquids which commonly referred to as black liquors and typically comprise organic solvents, solubilized lignins, solid and particulate monosaccarides, oligosaccharides, polysaccharides and other organic compounds released from the wood during the chemical digestion. The cellulosic fibrous pulps are typically used for paper manufacturing while the black liquors are usually processed to remove the soluble lignins after which, the organic solvents are recovered, purified and recycled. The lignins and remaining stillage from the black liquors are typically handled and disposed of as waste streams.

During the past two decades, those skilled in these arts have recognized that lignocellulosic materials including gymnosperm and angiosperm substrates (i.e., wood) as well as field crop and other herbaceous fibrous biomass, waste paper and wood containing products and the like, can be potentially fractionated using biorefining processes incorporating organosolv digestion systems, into multiple useful component parts that can be separated and further processed into high-value products such as fuel ethanol, lignins, furfural, acetic acid, purified monosaccharide sugars among others (Pan et al., 2005, Biotechnol. Bioeng. 90: 473-481; Pan et al., 2006, Biotechnol Bioeng. 94: 851-861; Berlin et al., 2007, Appl. Biochem. Biotechnol. 136-140:267-280; Berlin et al., 2007, J. Chem. Technol Biotechnol. 82: 767-774). Organosolv pulping processes and systems for lignocellulosic feedstocks are well-known and are exemplified by the disclosures in U.S. Pat. Nos. 4,941,944; 5,730,837; 6,179,958; and 6,228,177. Although it appears that biorefining using organosolv systems has considerable potential for large-scale fuel ethanol production, the currently available processes and systems are not yet economically feasible because they require expensive pretreatment steps and currently produce only low-value co-products (Pan et al., 2006, J. Agric. Food Chem. 54: 5806-5813; Berlin et al., 2007, Appl. Biochem. Biotechnol. 136-140:267-280; Berlin et al., 2007, J. Chem. Technol Biotechnol. 82: 767-774).

SUMMARY OF THE INVENTION

The exemplary embodiments of the present invention relate to systems, processes and equipment configurations for receiving and controllably commingling lignocellulosic feedstocks with counter-flowing organic solvents while providing suitable temperature and pressure conditions for fractionating the lignocellulosic feedstocks into component parts which are then subsequently separated. The separated component parts are further selectively, controllably and manipulably processed.

According to one exemplary embodiment of the present invention, there is provided a modular processing system for receiving therein and fractionating a lignocellulosic feedstock into component parts, separating the component parts into at least a solids fraction and a liquids fraction, and then separately processing the solids and liquids fractions to further produce useful products therefrom. Suitable modular processing systems of the present invention comprise at least:

a first module comprising a plurality of equipment configured for: (a) receiving and processing lignocellulosic fibrous feedstocks, then (b) commingling under controlled temperature and pressure conditions the processed feedstocks with suitable solvents configured for physico-chemically disrupting the lignocellulosic feedstock into a solids fraction comprising mostly cellulosic pulps and a liquid fraction comprising spent solvents containing therein at least lignins, lignin-containing compounds, monosaccharides, oligosaccharides and polysaccharides, dissolved and suspended solids comprising hemicelluloses and celluloses and other organic compounds, and (c) providing a first output stream comprising the solids fraction and a second output stream comprising the liquids fraction;

a second module comprising a plurality of equipment configured for: (d) receiving and controllably adjusting the viscosity of the solids fraction, (e) commingling the adjusted-viscosity solids fraction with suitable enzymes selected for saccharification of the cellulosic pulps into a liquid stream comprising monosaccharides and/or oligosaccharides (f) commingling the monosaccharides and/or oligosaccharides liquid stream with suitable fermenting microorganisms for production of an ethanol stream therefrom, (g) refining the ethanol to produce at least a fuel grade ethanol stream and de-alcoholized solvent stream, (h) further processing the de-alcoholized solvent-stillage stream to precipitate and separate a first lignin fraction therefrom, and (i) recycling the de-lignified de-alcoholized solvent stream for controllably adjusting the viscosity of fresh solids fraction coming into the second module from the first output stream of the first module;

a third module comprising a plurality of equipment configured for (j) receiving the liquids fraction from the first module and controllably intermixing a supply of water with the liquids fraction thereby precipitating a second lignin fraction therein, (k) separating the second lignin fraction from the liquids fraction thereby producing a liquid filtrate, (l) refining the liquid filtrate in a distillation tower thereby by capturing at least firstly, a portion of the suitable solvents commingled with the lignocellulosic feedstock in the first module, secondly, a furfural fraction, and thirdly, a stillage fraction, (m) controllably recharging the captured portion of the suitable solvents with a portion of the fuel ethanol produced in the second module; and a fourth module comprising a plurality of equipment configured for receiving the stillage fraction from the third module and separating therefrom at least acetic acid condensate, sugar syrups, a third lignin fraction, and a semi-solid/solid waste material.

According to one aspect, the plurality of equipment in the first module is configured to continuously receive and convey therethrough in one direction a lignocellulosic feedstock ending with the discharge of a cellulosic solids fraction, while concurrently counterflowing a selected suitable solvent through the equipment in an opposite direction to the conveyance of the lignocellulosic feedstock ending in a discharge of a spent solvents liquid fraction.

According to another aspect, the plurality of equipment in the first module is configured to receive a batch of a lignocellulosic feedstock and to continuously cycle therethrough a selected suitable solvent therethrough until a suitable solids fraction is produced from the batch of lignocellulosic feedstock.

According to yet another aspect, the plurality of equipment in the second module is configured to sequentially: (a) receive and reduce the viscosity of the cellulosic solids fraction discharged from the first module, then (b) progressively saccharify the cellulosic solids into suspended solids, dissolved solids, hemicelluloses, polysaccharides, oligosaccharides thereby producing a liquid stream primarily comprising monosaccharides, (c) ferment the liquid stream, (d) distill and refine the fermentation beer to separate the beer into at least a fuel-grade ethanol and/or other fuel alcohols such as butanol, and a stillage stream, (e) delignify the stillage stream, and (f) recycle the delignified stillage stream for reducing the viscosity of fresh incoming cellulosic solids fraction discharged from the first module.

According to a further aspect, the plurality of equipment in the second module may be optionally configured to sequentially: (a) receive and reduce the viscosity of the cellulosic solids fraction discharged from the first module, then (b) concurrently saccharify the cellulosic solids into monosaccharides while fermenting the monosaccharides in the same vessel, (c) distill and refine the fermentation beer to separate the beer into at least a fuel-grade ethanol and a stillage stream, (d) de-lignify the stillage stream, and (f) recycle the de-lignified stillage stream for reducing the viscosity of fresh incoming cellulosic solids fraction discharged from the first module.

According to another aspect, the modular processing system of the present system may be additionally provided with a fifth module comprising an anaerobic digestion system provided with a plurality of equipment configured for receiving the semi-solid/solid waste material from the fourth module, then liquifying and gasifying the waste material for the production of methane, carbon dioxide, and water.

According to another exemplary embodiment of the present invention, there is provided processes for fractionating a lignocellulosic feedstock into component parts. First, foreign materials exemplified by gravel and metal are separated using suitable means, from the incoming lignocellulosic material. An exemplary separating means is screening. If so desired, the screened lignocellulosic feedstock may be further screened to remove fines and over-size materials. Second, the screened lignocellulosic feedstock are controllably heated for example by steaming after which, the heated lignocellulosic feedstock is de-watered and then pressurized. Third, the heated and de-watered lignocellulosic feedstock is commingled and then impregnated with a suitable organic solvent. Fourth, the commingled lignocellulosic feedstock and organic solvent are controllably cooked within a controllably pressurized and temperature-controlled system for a selected period of time. During the cooking process, lignins and lignin-containing compounds contained within the commingled and impregnated lignocellulosic feedstock will be dissolved into the organic solvent resulting in the cellulosic fibrous materials adhered thereto and therewith to disassociate and to separate from each other. The cooking process will also release monosaccharides, oligosaccharides and polysaccarides and other organic compounds for example acetic acid, in solute and particulate forms, from the lignocellulosic materials into the organic solvents. Those skilled in these arts refer to such organic solvents containing therein lignins, lignin-containing compounds, monosaccharides, oligosaccharides and polysaccharides and other organic compounds, as "black liquors" or "spent liquors".

According to one aspect, controllably counter-flowing the organic solvent against the incoming lignocellulosic feedstock during the cooking causes turbulence that facilitates and speeds the dissolution and disassociation of the lignins and lignin-containing components from the lignocellulosic feedstock. However, it is within the scope of this invention to alternatively provide turbulence during the cooking process with a controllable flow of organic solvent directed in the same direction as the flow of lignocellulosic feedstock, i.e., a concurrent flow, thereby controllably intermixing the solvent and lignocellulosic feedstock together. It is also within the scope of this invention to controllably partially remove the organic solvent during the cooking process and to replace it with fresh organic solvent.

According to another aspect, the lignocellulosic feedstock may comprise at least one of physically disrupted angiosperm, gymnosperm, field crop fibrous biomass segments exemplified by chips, saw dust, chunks, shreds and the like. It is within the scope of this invention to provide mixtures of physically disrupted angiosperm, gymnosperm, field crop fibrous biomass segments.

According to yet another aspect, the lignocellulosic feedstock may comprise at least one of waste paper, wood scraps, comminuted wood materials, wood composites and the like. It is within the scope of this invention to intermix lignocellulosic fibrous biomass materials with one or more of waste paper, wood scraps, comminuted wood materials, wood composites and the like.

According to a further aspect, the liquor to wood ratio, operating temperature, solvent concentration and reaction time may be controllably and selectively adjusted to produce pulps and/or lignins having selectable target physico-chemical properties and characteristics.

According to another exemplary embodiment of the present invention, there are provided processes and systems for separating the disassociated cellulosic fibers i.e., pulp, from the black liquors, and for further and separately processing the pulp and the black liquors. The separation of pulp and black liquors may be done while the materials are still pressurized from the cooking process or alternatively, pressure may be reduced to about ambient pressure after which the pulp and black liquors are separated.

According to one aspect, the cellulosic fibrous pulp is recoverable for use in paper making and other such processes.

According to another aspect, there are provided processes and systems for further selectively and controllably processing the cellulosic pulps produced as disclosed herein. The pH and/or the consistency of the recovered pulp may be adjusted as suitable to facilitate the hydrolysis of celluloses to monosaccharides, i.e., glucose moieties in hydrolysate solutions. Exemplary suitable hydrolysis means include enzymatic, microbial, chemical hydrolysis and combinations thereof.

According to yet another aspect, there are provided processes and systems for producing ethanol from the monosaccarides hydrolyzed from the cellulosic fibrous pulp, by fermentation of the hydrolysate solutions. It is within the scope of this invention to controllably provide inocula comprising one or more selected strains of *Saccharomyces* spp. to facilitate and enhance the rates of fermentation and/or fermentation efficiencies and/or fermentation yields.

According to a further aspect, there are provided processes and systems for concurrently saccharifying and fermenting the cellulosic pulps produced as disclosed herein. It is within the scope of the present invention to controllably hydrolyze the cellulosic fibrous pulps into monosaccharides by providing suitable hydrolysis means exemplified by enzymatic, microbial, chemical hydrolysis and combinations thereof, while concurrently and controllably fermenting the monosaccharide moieties produced therein. It is within the scope of this invention to controllably provide inocula comprising one or more selected strains of *Saccharomyces* spp. to facilitate and enhance the rates of concurrent fermentation and/or fermentation efficiencies and/or fermentation yields.

According to a further aspect, there are provided processes and systems for further processing the ethanol produced from the fermentation of the hydrolysate solutions. Exemplary processes include concentrating and purifying the ethanol by distillation, and de-watering or dehydration by passing the ethanol through at least one molecular sieve.

According to a further exemplary embodiment of the present invention, there are provided processes and systems for recovering lignins and lignin-containing compounds from the black liquors. An exemplary process comprises cooling the black liquor immediately after separation from the cellulosic fibrous pulp, in a plurality of stages wherein each stage, heat is recovered with suitable heat-exchange devices and organic solvent is recovered using suitable solvent recovery apparatus as exemplified by evaporation and cooling devices. The stillage, i.e., the cooled black liquors from which at least some organic solvent has been recovered, are then further cooled, pH adjusted (e.g. increasing acidity) and then rapidly diluted with water to precipitate lignins and lignin-containing compounds from the stillage. The precipitated lignins are subsequently washed at least once and then dried.

According to one aspect, the de-lignified stillage is processed through a distillation tower to evaporate remaining organic solvent, and to concurrently separate and concentrate furfural. The remaining stillage is removed from the bottom of the distillation tower. It is within the scope of the present invention to optionally divert at least a portion of the de-lignified stillage from the distillation tower input stream into the ethanol production stream for producing ethanol therefrom. Alternatively or optionally, at least a portion of the remaining stillage removed from the bottom of the distillation tower may be diverted into the ethanol production stream for producing ethanol therefrom.

According to another aspect, the stillage recovered form the bottom of the solvent recovery column, is further processed by: (a) decanting to recover complex organic extractives as exemplified by phytosterols, oils and the like, and then (b) evaporating the decanted stillage to produce (c) a stillage evaporate/condensate comprising acetic acid, and (d) a stillage syrup containing therein dissolved monosaccharides. The stillage syrup may be decanted to recover (e) novel previously unknown low molecular weight lignins. The decanted stillage syrup may be optionally evaporated to recover dissolved sugars.

It is within the scope of this invention to further process the recovered organic solvent by purification and concentration steps to make the recovered organic solvent useful for recycling back into continuous incoming lignocellulosic feedstock.

According to one aspect, an organic solvent is intermixed and commingled with the lignocellulosic feedstock for a selected period of time to pre-treat the lignocellulosic feedstock prior to commingling and impregnation with the counter-flowing (or alternatively, concurrently flowing) organic solvent.

BRIEF DESCRIPTION OF THE DRAWINGS

The present invention will be described in conjunction with reference to the following drawings in which:

FIG. 7 shows plots illustrating the simultaneous saccharification and fermentation (SSF) of organosolv-pretreated aspen (*Populus tremuloides*) chips: (a) % theoretical yield of ethanol produced from the resultant aspen pulps vs. time, and (b) the ethanol concentration in beers vs. time, produced during SSF of the aspen pulps;

FIG. 8 shows plots illustrating the SSF of organosolv-pretreated British Columbian beetle-killed lodgepole pine (*Pinus contorta*) chips: (a) % theoretical yield of ethanol produced from the resultant beetle-killed lodgepole pine pulps vs. time, and (b) the ethanol concentration in beers vs. time, produced during SSF of the resultant beetle-killed lodgepole pine pulps; and FIG. 9 shows plots illustrating the simultaneous saccharification and fermentation (SSF) of organosolv-pretreated wheat straw and switchgrass lignocellulosic feedstocks: (a) % theoretical yield of ethanol produced from the resultant cellulosic pulps vs. time, and (b) the ethanol concentration in beers vs. time, produced during SSF of the cellulosic pulps.

DETAILED DESCRIPTION OF THE INVENTION

Exemplary embodiments of the present invention relate to systems, processes and equipment configurations for receiving and controllably commingling lignocellulosic feedstocks with counter-flowing organic solvents, thereby fractionating the lignocellulosic feedstocks into component parts which are then subsequently separated. The separated component parts are further selectively, controllably and manipulably processed. The exemplary embodiments of the present invention are particularly suitable for separating out from lignocellulosic feedstocks at least four structurally distinct classes of lignin component parts with each class comprising multiple derivative lignin compounds, while concurrently providing processes for converting other component parts into at least fuel-grade ethanol, furfurals, acetic acid, and monosaccharide and/or oligosaccharides sugar streams.

Figure 1:
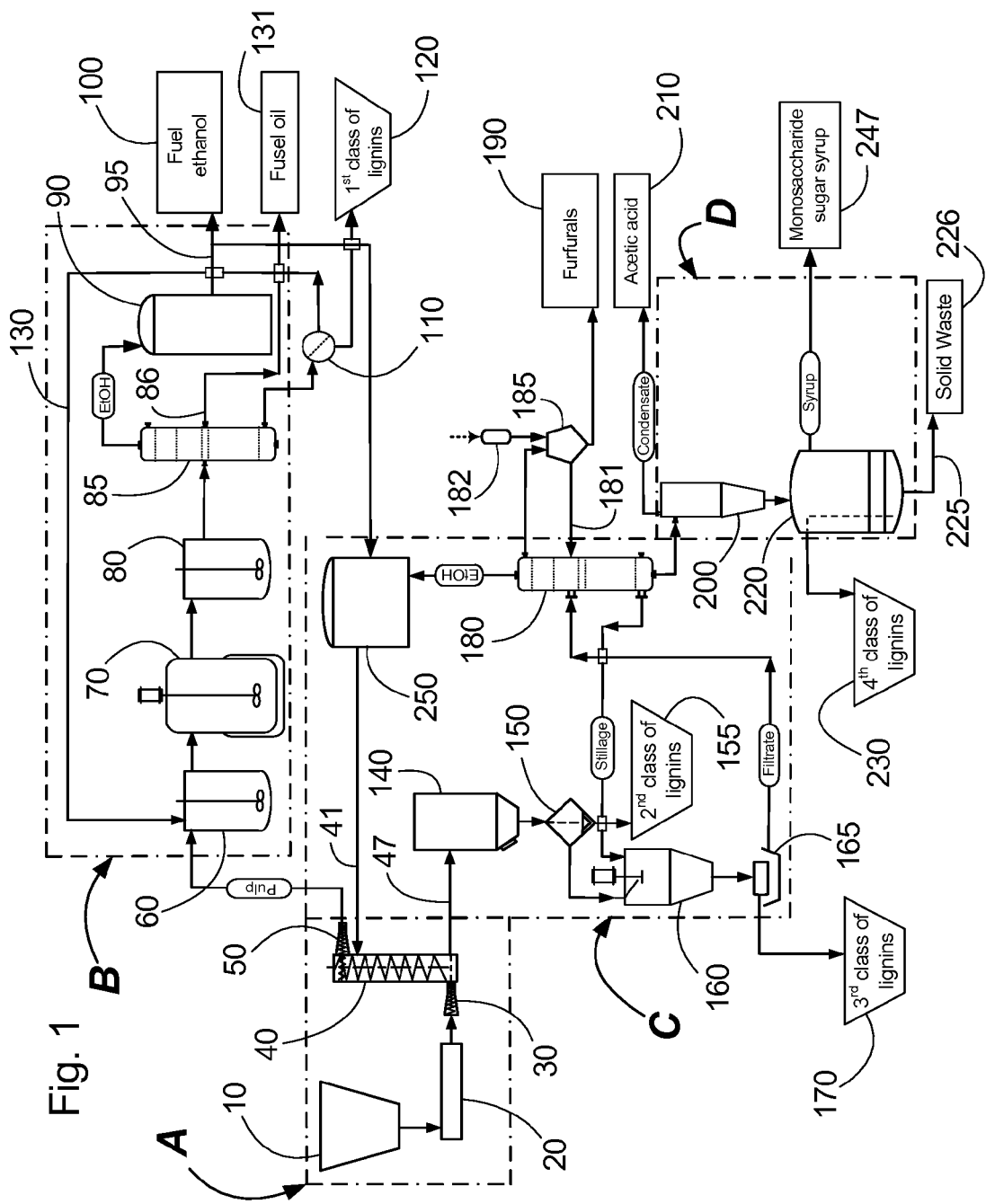
FIG. 1 is a schematic flowchart of an exemplary embodiment of the present invention of a modular continuous counter-flow system for processing a lignocellulosic feedstock.

An exemplary modular processing system of the present invention is shown in FIG. 1 and generally comprises four modules A-D wherein the first module A is configured for receiving and processing lignocellulosic feedstocks into a solids fraction and a liquids fraction, the second module B is configured for receiving the solids fraction discharged from the first module A and producing therefrom at least a fuel ethanol output stream 100 and a first class of lignin derivatives 120 referred to hereafter as a medium molecular weight lignin (i.e., MMW lignin), the third module C is configured for receiving the liquid fraction from the first module A and separating out at least a second class of lignin derivatives 170 referred to hereafter as high molecular weight lignins (i.e., HMW lignins), after which the filtrate is separated into at least recyclable distilled solvent, furfurals 190, and a stillage, and the fourth module D is configured for receiving and separating the stillage from the third module C into at least acetic acid 210, a third class of lignin derivatives 230 referred to hereafter as low molecular weight lignins (i.e., LMW lignins), a sugar syrup stream 247 from which is decanted and separated a fourth class of lignin derivatives 245 referred to hereafter as very-low molecular weight lignins (i.e., VLMW lignins), and a semi-solid/solid waste material 226.

The first module A as exemplified in FIG. 1 is provided with a bin 10 configured for receiving and temporarily storing lignocellulosic feedstocks while continually discharging the feedstock into a conveyance system provided with a separating device 20 configured for removing pebbles, gravel, metals and other debris. A suitable separating device is a screening apparatus. The separating device 20 may be optionally configured for sizing the lignocellulosic feedstock to desired fractions. The processed lignocellulosic feedstock is then conveyed with a first auger feeder 30 into a first end of a digestion/extraction vessel 40 and then towards the second end of the digestion/extraction vessel 40. The vessel 40 is provided with an inlet approximate the second end for receiving a pressurized stream of a suitable heated digestion/extraction solvent which then counterflows against the movement of the lignocellulosic feedstock through the vessel 40 thereby providing turbulence and commingling of the solvent with the feedstock. Alternatively, the inlet for receiving the pressurized stream of heated digestion/extraction solvent may be provided about the first end of the digestion/extraction vessel 40 or further alternatively, interposed the first and second ends of the digestion/extraction vessel 40. It is suitable to use organic solvents for the processes of the present invention. Exemplary suitable organic solvents include methanol, ethanol, propanol, butanol, acetone, and the like. If so desired, the organic solvents may be additionally controllably acidified with an inorganic or organic acid. If so desired, the pH of the organic solvents may be additionally controllably manipulated with an inorganic or organic base. The vessel 40 is controllably pressurized and temperature controlled to enable manipulation of pressure and temperature so that target cooking conditions are provided while the solvent is commingling with the feedstock. Exemplary cooking conditions include pressures in the range of about 15-30 bar (g), temperatures in the range of about 120-350° C., and pHs in the range of about 1.5-5.5. During the cooking process, lignins and lignin-containing compounds contained within the commingled and impregnated lignocellulosic feedstock will be dissolved into the organic solvent resulting in the cellulosic fibrous materials previously adhered thereto and therewith to disassociate and to separate from each other. Those skilled in these arts will understand that in addition to the dissolution of lignins and lignin-containing polymers, the cooking process will release monosaccharides, oligosaccharides and polysaccharides and other organic compounds for example acetic acid, furfural, 5-hydroxymethyl furfural (5-HMF), other organic acids such as formic and levulinic acids in solute and particulate forms, from the lignocellulosic materials into the organic solvents. Those skilled in these arts refer to such organic solvents containing the lignins, lignin-containing compounds, monosaccharides, oligosaccharides, polysaccharides, hemicelluloses and other organic compounds extracted from the lignocellulosic feedstock, as "black liquors" or "spent liquors". The disassociated cellulosic fibrous materials released from the feedstock are conveyed to the second end of the vessel 40 where they are discharged via a second auger feeder 50 which compresses the cellulosic fibrous materials into a solids fraction, i.e., a pulp which is then conveyed to the second module B. The black liquors are discharged as a liquid fraction from about the first end of the digestion/extraction vessel 40 into a pipeline 47 for conveyance to the third module C.

The second module B is provided with a mixing vessel 60 wherein the viscosity of solids fraction, i.e., pulp discharged from the first module A is controllably reduced to a selected target viscosity, by commingling with a recovered recycled solvent stream delivered by a pipeline 130 from a downstream component of module B. The reduced viscosity pulp is then transferred to a digestion vessel 70 where a suitable enzymatic preparation is intermixed and commingled with the pulp for progressively breaking down the cellulosic fibers, suspended solids and dissolved solids into hemicelluoses, polysaccharides, oligosaccharides and monosaccharides. A liquid stream comprising these digestion products is transferred from the digestion vessel 70 to a fermentation vessel 80 and is commingled with a suitable microbial inocula selected for fermentation of hexose and pentose monosaccharides in the liquid stream thereby producing a fermentation beer comprising at least a short-chain alcohol exemplified by ethanol, residual sediments and lees. The fermentation beer is transferred to a first distillation tower 90 for refining by volatilizing then distilling and separately collecting from the top of the distillation tower 90 at least a fuel-grade ethanol which is transferred and stored in a suitable holding container 100. The remaining liquid stillage is removed from the bottom of distillation tower 90 to equipment 110 configured to precipitate and separate MMW lignins which are then collected and stored in a suitable vessel 120 for further processing and/or shipment. It is within the scope of the present invention to heat the stillage and flash it with cold water to facilitate precipitation of the MMW lignins. The de-lignified stillage may then be controllably recycled from equipment 110 via pipeline 130 to the mixing vessel 60 for reducing the viscosity of fresh incoming pulp from the first module A.

Suitable enzyme preparations for addition to digestion vessel 70 for progressively breaking down cellulosic fibers into hemicelluloses, polysaccharides, oligosaccharides and monosaccharides may comprise one or more of enzymes exemplified by endo-β-1,4-glucanases, cellobiohydrolases, β-glucosidases, β-xylosidases, xylanases, α-amylases, β-amylases, pullulases, esterases, other hemicellulases and cellulases and the like. Suitable microbial inocula for fermenting pentose and/or hexose monosaccharides in fermentation vessel 80 may comprise one or more suitable strains selected from yeast species, fungal species and bacterial species. Suitable yeasts are exemplified by *Saccharomyces* spp. and *Pichia* spp. Suitable *Saccharomyces* spp are exemplified by *S. cerevisiae* such as strains Sc Y-1528, Tembec-1 and the like. Suitable fungal species are exemplified by *Aspergillus* spp. and *Trichoderma* spp. Suitable bacteria are exemplified by *Escherichia coli, Zymomonas* spp., *Clostridium* spp., and *Corynebacterium* spp. among others, naturally occurring and genetically modified. It is within the scope of the present invention to provide an inoculum comprising a single strain, or alternatively a plurality of strains from a single type of organism, or further alternatively, mixtures of strains comprising strains from multiple species and microbial types (i.e. yeasts, fungi and bacteria).

The black liquors discharged as a liquid fraction from the digestion/extraction vessel 40 of third module A, are processed in module C to recover at least a portion of the digestion/extraction solvent comprising the black liquors, and to separate useful components extracted from the lignocellulosic feedstocks as will be described in more detail below. The black liquors are transferred by pipeline 47 into a heating tower 140 wherein they are first heated and then rapidly mixed (i.e., "flashed") and commingled with a supply of cold water thereby precipitating HMW lignins from the black liquor. The precipitated HMW lignins are separated from the water-diluted black liquor by a suitable solids-liquids separation equipment 150 as exemplified by filtering apparatus, hydrocyclone separators, centrifuges and other such equipment. The separated HMW lignins are transferred to a lignin drier 160 for controlled removal of excess moisture, after which the dried HMW lignins are transferred to a storage bin 170 for packaging and shipping.

The de-lignified filtrate fraction is transferred from the separation equipment 150 to a second distillation tower 180 for vaporizing, distilling and recovering therefrom a short-chain alcohol exemplified by ethanol. The recovered short-chain alcohol is transferred to a digestion/extraction solvent holding tank 250 where it may, if so desired, be commingled with a portion of fuel-grade ethanol produced in module B and drawn from pipeline 95, to controllably adjust the concentration and composition of the digestion/extraction solvent prior to supplying the digestion/extraction solvent via pipeline 41 to the digestion/extraction vessel 40 of module A. It is within the scope of the present invention to recover furfurals from the de-lignified filtrate fraction concurrent with the vaporization and distillation processes within the second distillation tower, and transfer the recovered furfurals to a storage tank 190. An exemplary suitable process for recovering furfurals is to acidify the heated de-lignified filtrate thereby condensing furfurals therefrom. It is within the scope of the present invention to supply suitable liquid bases or acids to controllably adjust the pH of the de-lignified filtrate fraction. Suitable liquid bases are exemplified by sodium hydroxide. Suitable acids are exemplified by sulfuric acid.

The stillage from the second distillation tower is transferred to the fourth module D for further processing and separation of useful products therefrom. The hot stillage is transferred into a cooling tower 200 configured to collect a condensate comprising acetic acid which is then transferred to a suitable holding vessel 210. The de-acidified stillage is then transferred to a stillage processing vessel 220 configured for heating the stillage followed by flashing with cold water thereby precipitating LMW lignins which are then separated from a sugar syrup stream, and a semi-solid/solid waste material discharged into a waste disposal bin 226. The LMW lignins are transferred to a suitable holding container 230 for further processing and/or shipment. The sugar syrup stream, typically comprising at least one of xylose, arabinose, glucose, mannose and galactose, is passed through a decanter 240 which separates VLMW lignins from the sugar syrup stream thereby purifying the sugar syrup stream which is transferred to a suitable holding tank 247 prior to further processing and/or shipping, The VLMW lignins are transferred to a suitable holding tank 245 prior to further processing and/or shipping.

Figure 2:
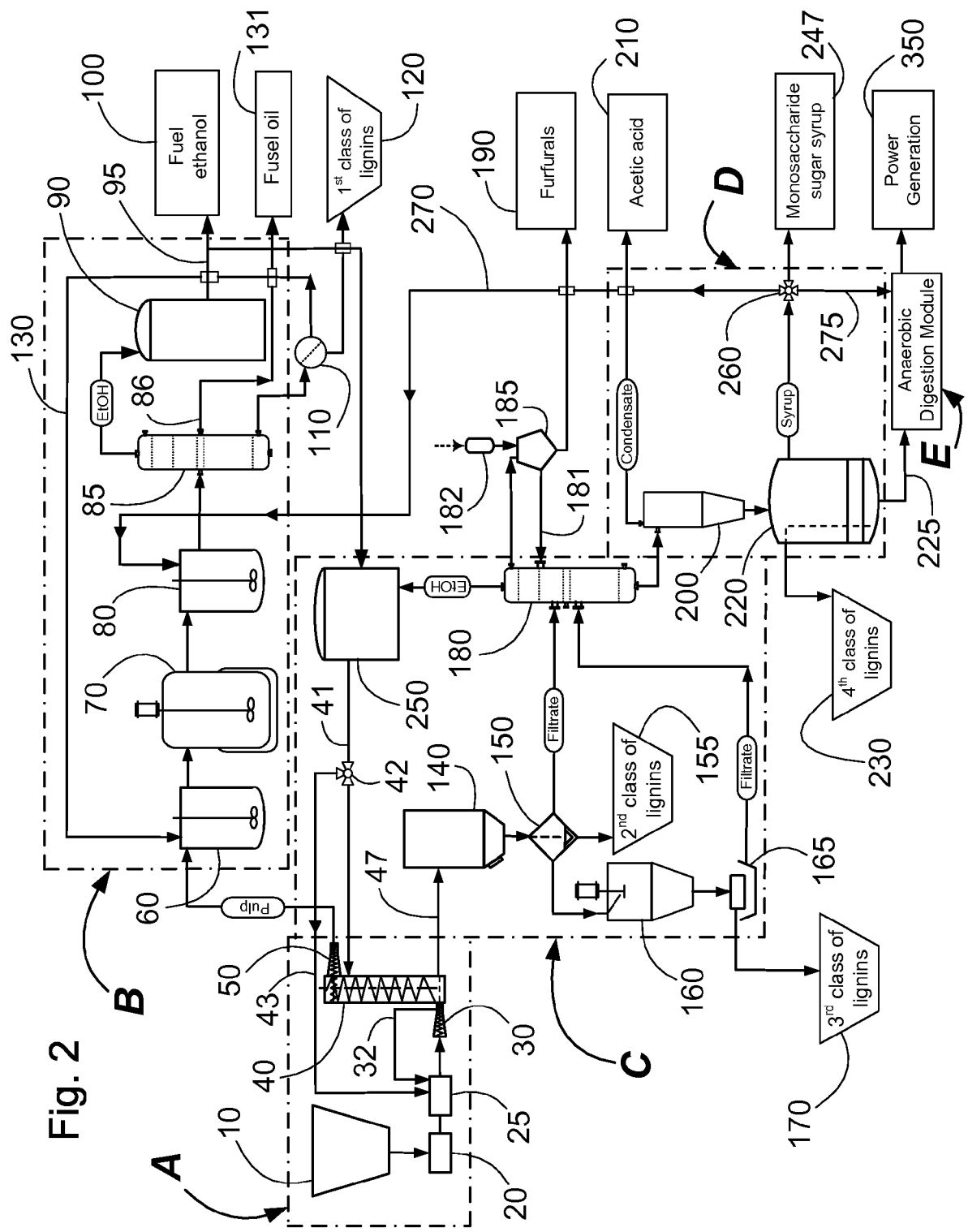
FIG. 2 is a schematic flowchart of the system from FIG. 1 additionally provided with a device for optionally diverting the sugar output stream to (a) the fuel ethanol production module, and (b) an anaerobic digestion module.

FIG. 2 illustrates exemplary modifications that are suitable for the modular lignocellulosic feedstock processing system of the present invention.

One exemplary embodiment includes provision of a pre-treatment vessel 25 for receiving therein processed lignocellulosic feedstock from the separating device 20 for pre-treatment prior to digestion and extraction by commingling and saturation with a heated digestion/extraction solvent for a suitable period of time. A suitable supply of digestion/extraction solvent may be diverted from pipeline 41 by a valve 42 and delivered to the pre-treatment vessel 25 by pipeline 43. Excess digestion/extraction solvent is squeezed from the processed and pre-treated lignocellulosic feedstock by the mechanical pressures applied by the first auger feeder 30 during transfer of the feedstock into the digestion/extraction vessel 40. The extracted digestion/extraction solvent is recyclable via pipeline 32 back to the pre-treatment vessel 25 for commingling with incoming processed lignocellulosic feedstock and fresh incoming digestion/extraction solvent delivered by pipeline 43. Such pre-treatment of the processed lignocellulosic feedstock prior to its delivery to the digestion/extraction vessel 40 will facilitate the rapid absorption of digestion/extraction solvent during the commingling and cooking process and expedite the digestion of the lignocellulosic feedstock and extraction of components therefrom.

Another exemplary embodiment illustrated in FIG. 2 provides a second diverter valve 260 interposed the sugar syrup stream discharged from the decanter 240 in module D. In addition to directing the sugar stream to the sugar stream holding tank 240, the second diverter valve 260 is configured for controllably diverting a portion of the liquid sugar stream into a pipeline 270 for delivery into the fermentation tank 80 in module B. Such delivery of a portion of the liquid sugar stream from module D will enhance and increase the rate of fermentation in tank 80 and furthermore, will increase the volume of fuel-grade ethanol produced from the lignocellulosic feedstock delivered to module A.

Figure 3:
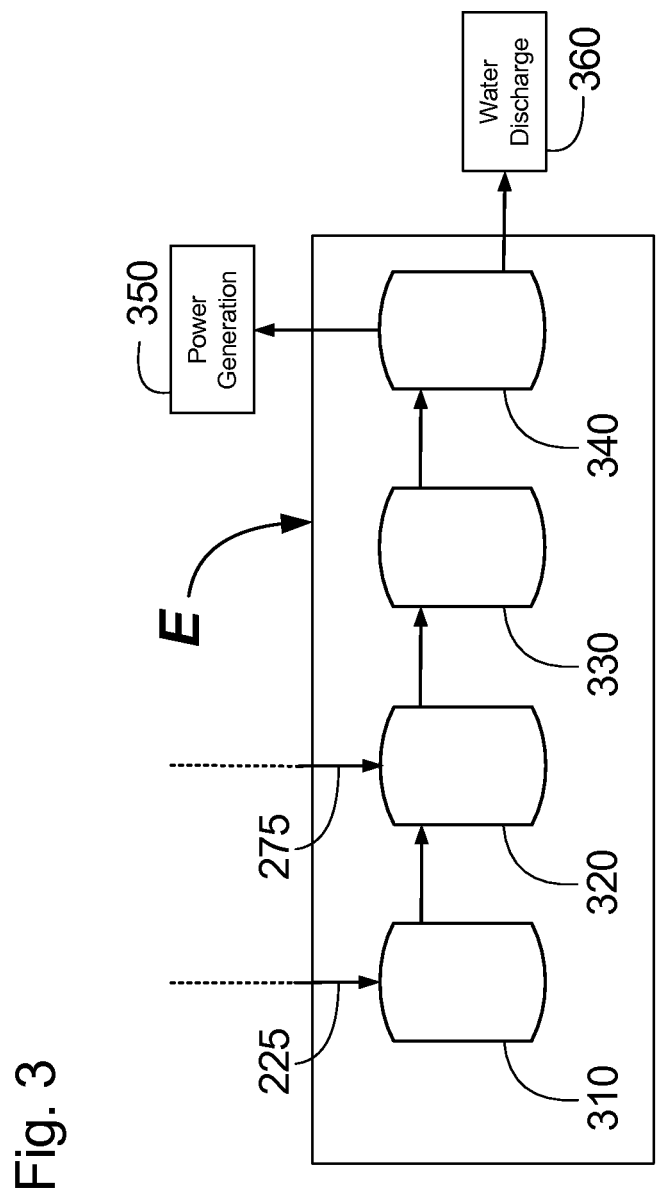
FIG. 3 is schematic flowchart showing an alternative configuration of the fuel ethanol production module for concurrent saccharification and fermentation processes within a single vessel.

Another exemplary embodiment illustrated in FIG. 2 provides an optional fifth module E comprising an anaerobic digestion system configured to receive semi-solid/solid wastes from the stillage processing vessel 220 and optionally configured for receiving a portion of the sugar syrup stream discharged from the stillage processing vessel 220. An exemplary anaerobic digestion system comprising module E of the present invention is illustrated in FIG. 3 and generally comprises a sludge tank 310, a vessel 320 configured for containing therein biological acidification processes (referred to hereinafter as an acidification vessel), a vessel 330 configured for containing therein biological acetogenesis processes (referred to hereinafter as an acetogenesis vessel), and a vessel 340 configured for containing therein biological processes for conversion of acetic acid into biogas (referred to hereinafter as a biogas vessel). The semi-solid/solid waste materials produced in the stillage processing vessel 220 of module C are transferred by a conveyance apparatus 225 to the sludge tank 310 wherein anaerobic conditions and suitable populations of facultative anaerobic microorganisms are maintained. Enzymes produced by the facultative microorganisms hydrolyze the complex organic molecules comprising the semi-solid/solid waste materials into soluble monomers such as monosaccharides, amino acids and fatty acids. It is within the scope of the present invention to provide if so desired inocula compositions for intermixing and commingling with the semi-solid/solid wastes in the sludge tank 310 to expedite the hydrolysis processes occurring therein. Suitable hydrolyzing inocula compositions are provided with at least one *Enterobacter* sp. A liquid stream containing therein the hydrolyzed soluble monomers is transferred into the acidification vessel 320 wherein anaerobic conditions and a population of acidogenic bacteria are maintained. The monosaccharides, amino acids and fatty acids contained in the liquid stream received by the acidification vessel 320 are converted into volatile acids by the acidogenic bacteria. It is within the scope of the present invention to provide if so desired acidification inocula compositions configured for facilitating and expediting the production of solubilized volatile fatty acids in the acidification tank 320. Suitable acidification inocula compositions are provided with at least one of *Bacillus* sp., *Lactobacillus* sp. and *Streptococcus* sp. A liquid stream containing therein the solubilized volatile fatty acids is transferred into the acetogenesis vessel 330 wherein anaerobic conditions and a population of acetogenic bacteria are maintained. The volatile fatty acids are converted by the acetogenic bacteria into acetic acid, carbon dioxide, and hydrogen. It is within the scope of the present invention to provide if so desired inocula compositions configured for facilitating and expediting the production of acetic acid from the volatile fatty acids delivered in the liquid stream into in the acetogenesis vessel 330. Suitable acetification inocula compositions are provided with at least one of *Acetobacter* sp., *Gluconobacter* sp., and *Clostridium* sp. The acetic acid, carbon dioxide, and hydrogen are then transferred from the acetogenesis vessel 330 into the biogas vessel 340 wherein the acetic acid is converted into methane, carbon dioxide and water. The composition of the biogas produced in the biogas vessel 330 of module E will vary somewhat with the chemical composition of the lignocellulosic feedstock delivered to module A, but will typically comprise primarily methane and secondarily $CO_2$, and trace amounts of nitrogen gas, hydrogen, oxygen and hydrogen sulfide. It is within the scope of the present invention to provide if so desired methanogenic inocula compositions configured for facilitating and expediting the conversion of acetic acid to biogas. Suitable methanogenic inocula compositions are provided with at least one of bacteria are from the *Methanobacteria* sp., *Methanococci* sp., and *Methanopyri* sp. The biogas can be fed directly into a power generation system as exemplified by a gas-fired combustion turbine. Combustion of biogas converts the energy stored in the bonds of the molecules of the methane contained in the biogas into mechanical energy as it spins a turbine. The mechanical energy produced by biogas combustion, for example, in an engine or micro-turbine may spin a turbine that produces a stream of electrons or electricity. In addition, waste heat from these engines can provide heating for the facility's infrastructure and/or for steam and/or for hot water for use as desired in the other modules of the present invention.

However, a problem with anaerobic digestion of semi-solid/solid waste materials is that the first step in the process, i.e., the hydrolysis of complex organic molecules comprising the semi-solid/solid waste materials into a liquid stream containing soluble monomers such as monosaccharides, amino acids and fatty acids, is typically lengthy and variable, while the subsequent steps, i.e., acidification, acetification, and biogas production proceed relatively quickly in comparison to the first step. Consequently, such lengthy and variable hydrolysis in the first step of anaerobic may result in insufficient amounts of biogas production relative to the facility's requirements for power production and/or steam and/or hot water. Accordingly, another embodiment of the present invention, as illustrated in FIGS. 2 and 3, controllably provides a portion of the sugar syrup stream discharged from the stillage processing vessel 220 of module D, to the acidification tank 320 of module E to supplement the supply of soluble monosaccharides hydrolyzed from semi-solid/solid materials delivered to the sludge tank 310. Thus, the amount of biogas produced by module E of the present invention can be precisely manipulated and modulated by providing a second diverter 260 interposed the sugar syrup discharge line from stillage processing vessel 220, to controllably divert a portion of the sugar syrup into pipeline 275 for transfer to the acidification vessel 320.

Figure 4:
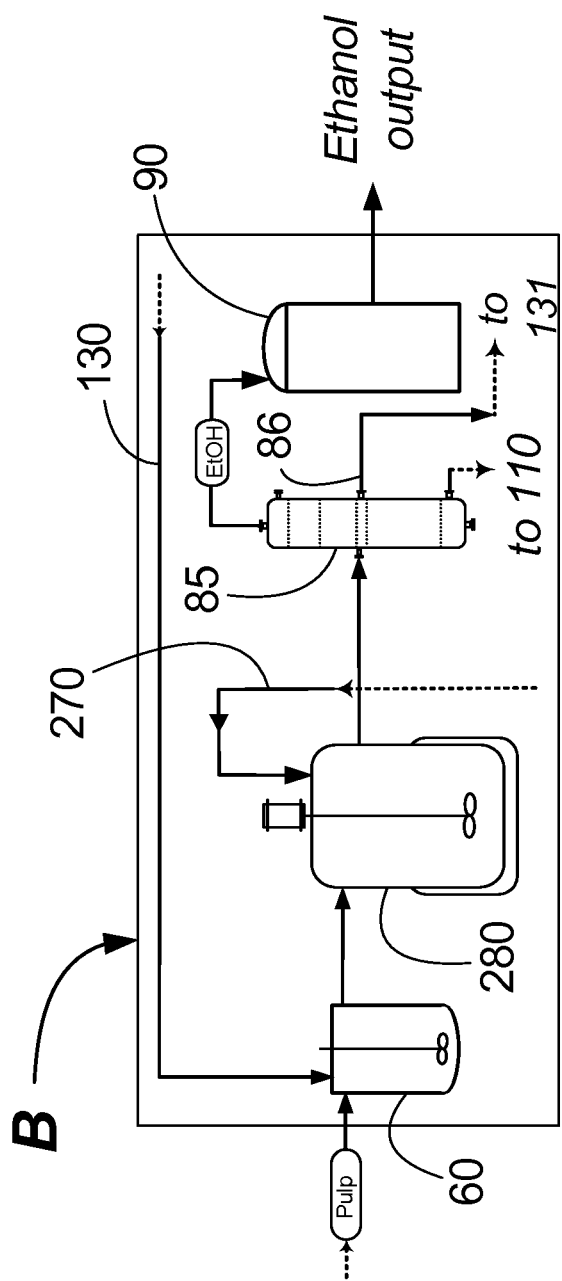
FIG. 4 is a schematic flowchart of an exemplary anaerobic digestion module suitable for cooperating with the modular continuous counter-flow system of the present invention for processing a lignocellulosic feedstock.

Another exemplary embodiment of the present invention is illustrated in FIG. 4 and provides an optional vessel 280 for module B, wherein vessel 280 is configured for receiving the reduced viscosity pulp from mixing vessel 60 (FIG. 2) and for concurrent i.e., co-saccharification and co-fermentation therein of the reduced-viscosity solids fractions. Those skilled in these arts will understand that such co-saccharification and co-fermentation processes are commonly referred to as "simultaneous saccharification and fermentation" (SSF) processes, and that vessel 280 (referred to hereinafter as a SSF vessel) can replace digestion vessel 70 and fermentation vessel 80 from FIG. 2. It is suitable to provide a supplementary stream of sugar syrup into the SSF vessel 280 via pipeline 270 from the second diverter valve 260 (FIGS. 2 and 4) to controllably enhance and increase the rate of fermentation in the SSF vessel 280.

Figure 5:
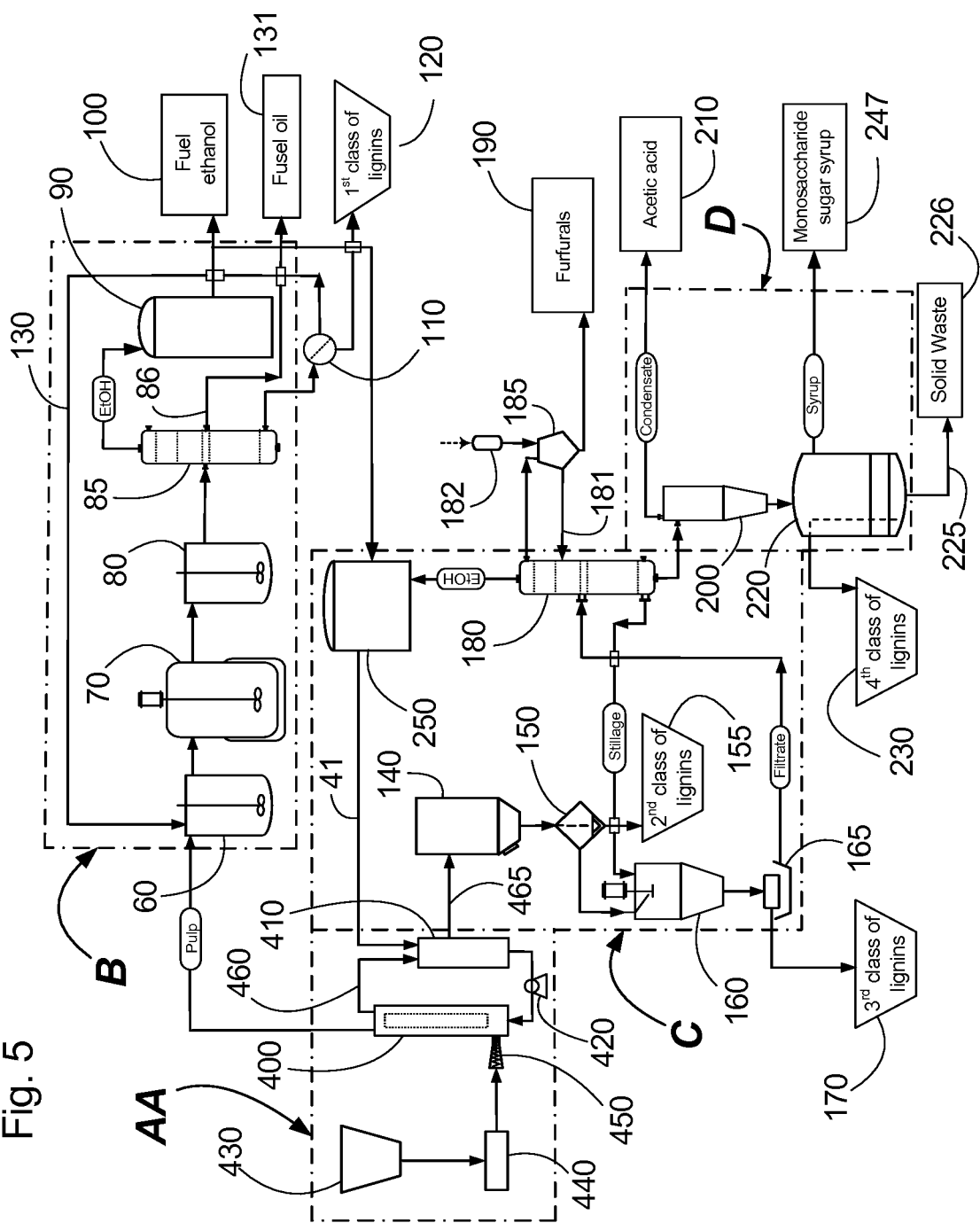
FIG. 5 is a schematic flowchart of a continuous counter-flow processing system of the process re-configured into a batch through-put system.

Another exemplary embodiment of the present invention is illustrated in FIG. 5 and provides an alternative first module AA, for communication and cooperation with modules B and C, wherein the alternative first module AA (FIG. 5) is configured for receiving, processing and digestion/extraction of batches of a lignocellulosic feedstock, as compared to module A which is configured for continuous inflow, processing and digestion/extraction of a lignocellulosic feedstock (FIG. 1). As shown in FIG. 5, one exemplary embodiment for batch digestion/extraction of a lignocellulosic feedstock comprises a batch digestion/extraction vessel 400 interconnected and communicating with a digestion/extraction solvent re-circulating tank 410 and a solvent pump 420. A batch of lignocellulosic feedstock is loaded into a receiving bin 430 from where it is controllably discharged into a conveyance system provided with a screening device 440 configured for removing pebbles, gravel, metals and other debris. The screening device 440 may be optionally configured for sizing the lignocellulosic feedstock into desired fractions. The processed lignocellulosic feedstock is then conveyed with a third auger feeder 450 into a first end of the batch digestion/extraction vessel 400. The digestion/extraction solvent re-circulating tank 410 is configured to receive a suitable digestion/extraction solvent from the digestion/extraction solvent holding tank 250 of module B via pipeline 41. The digestion/extraction solvent is pumped via solvent pump 420 into the batch digestion/extraction vessel 400 wherein it controllably commingled, intermixed and circulated through the batch of lignocellulosic feedstock contained therein. The batch digestion/extraction vessel 400 is controllably pressurized and temperature controlled to enable manipulation of pressure and temperature so that target cooking conditions are provided while the solvent is commingling and intermixing with the feedstock. Exemplary cooking conditions include pressures in the range of about 15-30 bar(g), temperatures in the range of about 120°-350° C., and pHs in the range of about 1.5-5.5. During the cooking process, lignins and lignin-containing compounds contained within the commingled and impregnated lignocellulosic feedstock will be dissolved into the organic solvent resulting in the cellulosic fibrous materials adhered thereto and therewith to disassociate and to separate from each other. Those skilled in these arts will understand that in addition to the dissolution of lignins and lignin-containing polymers, the cooking process will release monosaccharides, oligosaccharides and polysaccharides and other organic compounds for example acetic acid, in solute and particulate forms, from the lignocellulosic materials into the organic solvents. It is suitable to discharge the digestion/extraction solvent from the batch digestion/extraction vessel 400 through pipeline 460 during the cooking process for transfer via pipeline 460 back to the digestion/extraction solvent re-circulating tank 410 for re-circulation by the solvent pump 420 back into the batch digestion/extraction vessel 400 until the lignocellulosic feedstock is suitable digested and extracted into a solids fraction comprising a viscous pulp material comprising dissociated cellulosic fibers, and a liquids fraction, i.e., black liquor, comprising solubilized lignins and lignin-containing polymers, hemicelluloses, polysaccharides, oligosaccharides, monosaccharides and other organic compounds in solute and particulate forms, from the lignocellulosic materials in the spent organic solvents. It is within the scope of the present invention to withdraw a portion of the re-circulating digestion/extraction solvent from the solvent re-circulating tank 410 via pipeline 465 for transfer to the heating tower 140 in module C, and to replace the withdrawn portion of re-circulating digestion/extraction solvent with fresh digestion/extraction solvent from the digestion/extraction solvent holding tank 250 of module B via pipeline 41, thereby expediting the digestion/extraction processes within the batch digestion/extraction vessel 400. After digestion/extraction of the lignocellulosic feedstock has been completed, the solids fraction comprising cellulosic fibre pulp is discharged from the batch digestion/extraction vessel 400 and conveyed to the mixing vessel 60 in module B wherein the viscosity of the solids fraction, i.e., pulp discharged from the first module AA, is controllably reduced to a selected target viscosity by commingling and intermixing with de-lignified stillage delivered via pipeline 130 then be controllably recycled from de-lignification equipment 110 of module B after which the reduced-viscosity pulp is further processed by saccharification, fermentation and refining as previously described. The black liquor is transferred from the digestion/extraction solvent re-circulating tank 410 via pipeline 465 to the heating tower 140 in module C for precipitating lignin therefrom and further processing as previously described.

Figure 6:
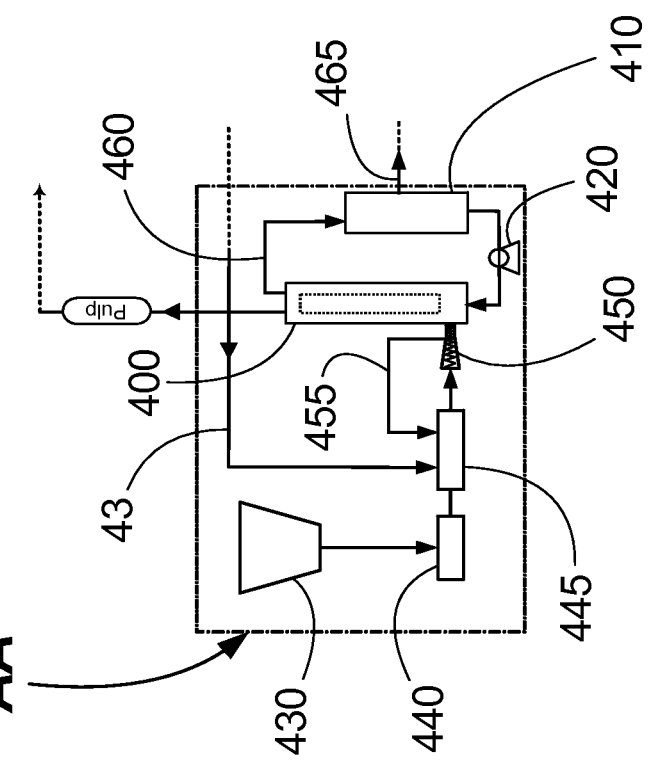
FIG. 6 is a schematic flowchart showing an alternative configuration for the batch throughput system shown in FIG. 5.

A suitable exemplary modification of the batch digestion/extraction module component of the present invention is illustrated in FIG. 6, wherein a pre-treatment vessel 445 is provided for receiving therein processed lignocellulosic feedstock from the screening device 440 for pre-treatment prior to conveyance to the batch digestion/extraction vessel 400, by commingling and saturation with a digestion/extraction solvent for a suitable period of time. A suitable supply of digestion/extraction solvent may be diverted from pipeline 41 by a valve 42 (shown in FIG. 2) and delivered to the pre-treatment vessel 445 by pipeline 43. Excess digestion/extraction solvent is squeezed from the processed and pre-treated lignocellulosic feedstock by the mechanical pressures applied by the third auger feeder 450 during transfer of the feedstock into the batch digestion/extraction vessel 400. The extracted digestion/extraction solvent is recyclable via pipeline 455 back to the pre-treatment vessel 445 for commingling with incoming processed lignocellulosic feedstock and fresh incoming digestion/extraction solvent delivered by pipeline 43. Such pre-treatment of the processed lignocellulosic feedstock prior to its delivery to the batch digestion/extraction vessel 400 will facilitate the rapid absorption of digestion/extraction solvent during the commingling and cooking process and expedite the digestion of the lignocellulosic feedstock and extraction of components therefrom.

The systems, methods and processes for fractionating lignocellulosic feedstocks into component parts which are then subsequently separated are described in more detail in the following examples with a selected hardwood and a selected softwood species. The following examples are intended to be exemplary of the invention and are not intended to be limiting.

Example 1

Representative samples of whole logs of British Columbian aspen (*Populus tremuloides*) (~125 years old) were collected. After harvesting, logs were debarked, split, chipped, and milled to a chip size of approximately $\leq$10 mm×10 mm×3 mm. Chips were stored at room temperature (moisture content at equilibrium was ~10%). The aspen chips were organosolv-pretreated in aqueous ethanol (50% w/w ethanol) with no addition of exogenous acid or base, in a 2-L PARR® reactor (Parr is a registered trademark of the Parr Instrument Company, Moline, Ill., USA). Duplicate 200 g (ODW) samples of the aspen chips, designated as ASP1, were cooked at 195° C. for 60 min. The liquor:wood ratio was 5:1 weight-based. After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of washed and unwashed pulps was determined according to a modified Klason lignin method derived from the Technical Association of Pulp and Paper Industry (TAPPI) standard method T222 om-88 (TAPPI methods in CD-ROM, 2004, TAPPI Press). Liquids were analyzed for carbohydrate degradation products (furfural, 5-hydromethylfurfural), acids, and oligo- and monosaccharides according to standard procedures established by the National Renewable Energy Laboratory (NREL, Golden, Colo., USA). The resulting data were used to calculate overall lignin and carbohydrate recoveries and process mass balance. The carbohydrate composition and overall carbohydrate recoveries from the raw and pretreated aspen chips are shown in Table 1. 222.2 g (oven-dried weight, odw) of ASP1 pulp were recovered after batch organosolv processing of 400 g of aspen wood chips (55.6% pulp yield) containing mainly fermentable-into-ethanol carbohydrates. Pentoses and hexoses were partially degraded resulting in 0.71 g $Kg^{-1}$ of furfural and 0.06 g $Kg^{-1}$ of 5-HMF, respectively. The different classes of lignins recovered from the pulp and liquors are shown in Table 2.

TABLE 1

Carbohydrate content of raw and pretreated aspen chips (ASP1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0.04 | 0.17 | 0.21 | 9.69 | 2.53 | 12.23 |
| Galactan | 0.43 | 1.71 | 0.16 | 0.26 | 0.42 | 15.16 | 9.07 | 24.23 |
| Glucan | 48.76 | 195.03 | 185.40 | 0.32 | 185.72 | 0.16 | 95.06 | 95.23 |
| Xylan | 16.44 | 65.75 | 17.60 | 8.70 | 26.30 | 13.23 | 26.77 | 40.00 |
| Mannan | 1.48 | 5.92 | 4.62 | 0 | 4.62 | 0 | 78.02 | 78.02 |
| Total: | 67.55 | 270.16 | 207.82 | 9.45 | 217.27 | | | |

TABLE 2

Lignin input in raw aspen chips and lignin fractions recovered after organosolv pretreatment (ASP1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (MMW) | — | — | 9.60 |
| Precipitated lignin* (LMW) | — | — | 32.12 |
| Very low molecular wt. lignin (VLMW) | — | — | 11.72 |
| Residual lignin (HMW) | — | 11.33 | — |
| Total: | 91.35 | 11.33 | 53102.68 |

*recovered from the liquor by precipitation with water; AIL - acid-insoluble lignin; ASL - acid-soluble lignin The potential of the washed pulp for production of ethanol was evaluated in 100-mL Erlenmeyer flasks. The pH of the washed pulp was first adjusted with a water ammonia solution to pH 5.50, then placed into Erlenmeyer flasks and resuspended in distilled water to a total reaction weight of 100 g (including the yeast and enzyme weight, the final reaction volume was ~100 mL) and a final solids concentration of 16% (w/w). The ethanol production process was run according to a simultaneous saccharification and fermentation scheme (SSF) using a commercial *Trichoderma reesei* fungal cellulase preparation CELLUCLAST® 1.5 L (Celluclast is a registered trademark of Novozymes A/S Corp., Bagsvaerd, Denmark) at 15 FPU g$^{-1}$ glucan supplemented with a commercial beta-glucosidase preparation (30 CBU g$^{-1}$ glucan) and a ethanologenic yeast, *Saccharomyces cerevisiae* strain Y-1528 (available from the Agricultural Research Service, United States Department of Agriculture, Peoria, Ill., USA) at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 39.40% theoretical ethanol yield based on initial hexose input. The final ethanol beer concentration was 3.26% (w/w) (FIGS. 7a and 7b).

Example 2

Duplicate 200-g samples of the wood chips prepared in Example 1, designated as ASP2, were used for this study. The aspen chips were organosolv-pretreated in aqueous ethanol (50% w/w ethanol) with no addition of exogenous acid or base, in a 2-L PARR® reactor. Duplicate 200 g (ODW) samples of aspen chips were cooked at 195° C. for 90 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88 (TAPPI methods in CD-ROM, 2004, TAPPI Press). Liquids were analyzed for carbohydrate degradation products (furfural, 5-hydromethylfurfural), acids, and oligo- and monosaccharides according to standard procedures established by the National Renewable Energy Laboratory (NREL, Golden, Colo., USA). The resulting data were used to calculate overall carbohydrate and lignin recoveries and process mass balance. The carbohydrate composition and overall carbohydrate recoveries from the raw and pretreated aspen chips are shown in Table 3. 230.2 g (odw) of pulp were recovered after batch organosolv processing of 400 g of aspen wood chips (57.6% pulp yield), and comprised mainly fermentable-into-ethanol carbohydrates. Pentoses and hexoses were partially degraded resulting in 0.53 g Kg$^{-1}$ of furfural and 0.05 g Kg$^{-1}$ of 5-HMF, respectively. The lignin content in the raw aspen chips and overall lignin recovery after pretreatment are shown in Table 4.

TABLE 3

Carbohydrate content of raw and pretreated aspen chips (ASP2 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0 | 0.22 | 0.22 | 12.54 | 0.00 | 12.54 |
| Galactan | 0.43 | 1.71 | 0 | 0.21 | 0.21 | 12.25 | 0.00 | 12.25 |
| Glucan | 48.76 | 195.03 | 194.50 | 0.37 | 194.87 | 0.19 | 99.73 | 99.92 |
| Xylan | 16.44 | 65.75 | 14.80 | 6.76 | 21.56 | 10.28 | 22.51 | 32.79 |
| Mannan | 1.48 | 5.92 | 4.07 | 0.34 | 4.41 | 5.74 | 68.78 | 74.52 |
| Total: | 67.55 | 270.16 | 213.37 | 7.9 | 221.27 | | | |

TABLE 4

Lignin input in raw aspen chips and lignin fractions recovered after organosolv pretreatment (ASP2 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (MMW) | — | — | 9.14 |
| Precipitated lignin* (LMW) | — | — | 43.09 |
| Very low molecular wt. lignin (VLMW) | — | — | 12.60 |
| Residual lignin (HMW) | — | 7.32 | — |
| Total: | 91.35 | 7.32 | 64.83 |

*recovered from the liquor by precipitation with water; AIL - acid-insoluble lignin; ASL - acid-soluble lignin Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, then placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF using a commercial Trichoderma reesei fungal cellulase preparation CELLUCLAST® 1.5 L at 15 FPU $g^{-1}$ glucan supplemented with a commercial beta-glucosidase preparation (30 CBU $g^{-1}$ glucan) and an ethanologenic yeast, Saccharomyces cerevisiae strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 79.30% theoretical ethanol yield based on initial hexose input. The final ethanol beer concentration was 6.33% (w/w) (FIGS. 7a and 7b).

Example 3

Duplicate 200-g samples of the wood chips prepared in Example 1, designated as ASP3, were used for this study. The aspen chips were organosolv-pretreated in aqueous ethanol (50% w/w ethanol) with no addition of exogenous acid or base, in a 2-L PARR® reactor. The duplicate samples of aspen chips were cooked in duplicate at 195° C. for 120 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and overall carbohydrate recoveries from the raw and pretreated aspen chips are shown in Table 5. 219.9 g (odw) of pulp were recovered after batch organosolv processing of 400 g of aspen wood chips (54.98% pulp yield) containing mainly fermentable-into-ethanol carbohydrates. Pentoses and hexoses were partially degraded resulting in 0.92 g $Kg^{-1}$ of furfural and 0.08 g $Kg^{-1}$ of 5-HMF, respectively. The lignin contents in raw aspen chips and overall lignin recovery after pretreatment are shown in Table 6.

Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF scheme using a commercial Trichoderma reesei fungal cellulase preparation CELLUCLAST® 1.5 L at 15 FPU $g^{-1}$ glucan supplemented with a commercial beta-glucosidase preparation (30 CBU $g^{-1}$ glucan) and an ethanologenic yeast, Saccharomyces cerevisiae strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 79.00% theoretical ethanol yield based on initial hexose input. The final ethanol beer concentration was 6.60% (w/w) (FIGS. 7a and 7b).

TABLE 5

Carbohydrate content of raw and pretreated aspen chips (ASP3 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 0.44 | 1.75 | 0 | 0.10 | 0.10 | 5.70 | 0 | 5.70 |
| Galactan | 0.43 | 1.71 | 0 | 0.15 | 0.15 | 8.75 | 0 | 8.75 |
| Glucan | 48.76 | 195.03 | 186.63 | 0.33 | 186.96 | 0.17 | 95.69 | 95.86 |
| Xylan | 16.44 | 65.75 | 12.56 | 4.03 | 16.59 | 6.13 | 19.10 | 25.23 |
| Mannan | 1.48 | 5.92 | 3.50 | 0.30 | 3.80 | 5.06 | 59.02 | 64.08 |
| Total: | 67.55 | 270.16 | 202.69 | 4.91 | 207.6 | | | |

TABLE 6

Lignin input in raw aspen chips and lignin fractions recovered after organosolv pretreatment (ASP3 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 91.35 | — | — |
| Self-precipitated lignin (MMW) | — | — | 0.16 |
| Precipitated lignin* (LMW) | — | — | 40.70 |
| Very low molecular wt. lignin (VLMW) | — | — | 11.46 |
| Residual lignin (HMW) | — | 6.47 | — |
| Total: | 91.35 | 6.47 | 5297.8232 |

*recovered from the liquor by precipitation with water; AIL - acid-insoluble lignin; ASL - acid-soluble lignin Example 4

Representative samples of British Columbian beetle-killed lodgepole pine (*Pinus contorta*) sapwood (~120 years old) were collected. After harvesting, logs were debarked, split, chipped, and milled to a chip size of approximately ≦10 mm×10 mm×3 mm. Chips were stored at room temperature (moisture content at equilibrium was ~10%). Duplicate 200-g samples of these wood chips, designated as BKLLP1, were used for this study. The chips were organosolv-pretreated in aqueous ethanol (50% w/w ethanol) with addition of 1.10% (w/w) sulfuric acid, in a 2-L PARR® reactor. The chips were cooked in duplicate at 170° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydroxymethylfurfural), acids, and oligo- and monosaccharides according to standard procedures established by the National Renewable Energy Laboratory. The obtained data were used to calculate overall carbohydrate and lignin recoveries and process mass balance. The carbohydrate composition and the overall carbohydrate recoveries from the raw and pretreated beetle-killed lodgepole pine chips are shown in Table 7. 177.2 g (odw) of pulp were recovered after batch organosolv processing of 400 g of wood chips (44.30% pulp yield) containing mainly fermentable-into-ethanol carbohydrates. Pentoses and hexoses were partially degraded resulting in 0.72 g Kg$^{-1}$ of furfural and 1.78 g Kg$^{-1}$ of 5-HMF, respectively. The lignin content in raw beetle-killed lodgepole pine chips and overall lignin recovery after pretreatment are shown in Table 8.

TABLE 7

Carbohydrate content of raw and pretreated beetle-killed lodgepole pine chips (BKLLP1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.05 | 0.77 | 0.82 | 10.96 | 0.76 | 11.72 |
| Galactan | 2.01 | 8.05 | 0.35 | 1.25 | 1.60 | 15.52 | 4.40 | 19.92 |
| Glucan | 45.55 | 182.22 | 150.44 | 4.37 | 154.81 | 2.40 | 82.56 | 84.96 |
| Xylan | 7.22 | 28.90 | 3.58 | 1.64 | 5.22 | 5.68 | 12.39 | 18.07 |
| Mannan | 11.07 | 44.29 | 6.06 | 0.00 | 6.06 | 0.00 | 13.68 | 13.68 |
| Total: | 67.61 | 270.49 | 160.48 | 8.03 | 168.51 | | | |

TABLE 8

Lignin input in raw beetle-killed lodgepole pine chips and lignin fractions recovered after organosolv pretreatment (BKLLP1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (MMW) | — | — | 0.17 |
| Precipitated lignin* (LMW) | — | — | 28.10 |
| Very low molecular wt. lignin (VLMW) | — | — | 13.47 |
| Residual lignin (HMW) | — | 15.29 | — |
| Total: | 106.85 | 15.29 | 41.74 |

*recovered from the liquor by precipitation with water; AIL - acid-insoluble lignin; ASL - acid-soluble lignin Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a simultaneous saccharification and fermentation scheme (S SF) using a commercial *Trichoderma reesei* fungal cellulase preparation CELLUCLAST® 1.5 L at 15 FPU $g^{-1}$ glucan supplemented with a commercial beta-glucosidase preparation (30 CBU $g^{-1}$ glucan) together with an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 60.50% theoretical ethanol yield based on initial hexose input. The final ethanol beer concentration was 7.18% (9 w/w) (FIGS. 8a and 8b).

Example 5

Duplicate 200-g samples British Columbian beetle-killed lodgepole pine (*Pinus contorta*), designated as BKLLP2, of the chips prepared for the study described in the Example 4, were organosolv-pretreated in aqueous ethanol (50% w/w ethanol) with addition of 1.10% (w/w) sulphuric acid, in a 2-L PARR® reactor. Duplicate 200-g (ODW) samples of chips were cooked at 175° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated beetle-killed lodgepole pine chips are shown in Table 9. 144.4 g (odw) of pulp were recovered after batch organosolv processing of 400 g of wood chips (36.10% pulp yield) containing mainly fermentable-into-ethanol carbohydrates. Pentoses and hexoses were partially degraded resulting in 0.92 g $Kg^{-1}$ of furfural and 1.87 g $Kg^{-1}$ of 5-HMF, respectively. The lignin content in raw beetle-killed lodgepole pine chips and overall lignin recovery after pretreatment are shown in Table 10.

TABLE 9

Carbohydrate content of raw and pretreated beetle-killed lodgepole pine chips (BKLLP2 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.04 | 0.39 | 0.43 | 5.55 | 0.62 | 6.17 |
| Galactan | 2.01 | 8.05 | 0.03 | 0.79 | 0.82 | 9.81 | 0.36 | 10.17 |
| Glucan | 45.55 | 182.22 | 134.08 | 5.28 | 139.36 | 2.90 | 73.58 | 76.48 |
| Xylan | 7.22 | 28.90 | 1.59 | 0.65 | 2.24 | 2.25 | 5.50 | 7.75 |
| Mannan | 11.07 | 44.29 | 2.30 | 0 | 2.30 | 0 | 5.18 | 5.18 |
| Total: | 67.61 | 270.49 | 138.04 | 7.11 | 145.15 | | | |

TABLE 10

Lignin input in raw beetle-killed lodgepole pine chips and lignin fractions recovered after organosolv pretreatment (BKLLP2 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (MMW) | — | — | 0.13 |
| Precipitated lignin* (LMW) | — | — | 33.01 |
| Very low molecular wt. lignin (VLMW) | — | — | 11.88 |
| Residual lignin (HMW) | — | 7.15 | — |
| Total: | 106.85 | 7.15 | 45.02 |

*recovered from the liquor by precipitation with water; AIL - acid-insoluble lignin; ASL - acid-soluble lignin Production of ethanol from the washed pulp was evaluated in 100-mL Erlenmeyer flasks. The experiments were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a simultaneous saccharification and fermentation scheme (S SF) using a commercial Trichoderma reesei fungal cellulase preparation CELLUCLAST® 1.5 L at 15 FPU $g^{-1}$ glucan supplemented with a commercial beta-glucosidase preparation (30 CBU $g^{-1}$ glucan) and an ethanologenic yeast, Saccharomyces cerevisiae strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 53.10% theoretical ethanol yield based on initial hexose input. The final ethanol beer concentration was 7.74% (w/w) (FIGS. 8a and 8b).

Example 6

Duplicate 200-g samples British Columbian beetle-killed lodgepole pine (Pinus contorta), designated as BKLLP3, chips prepared for the study described in the Example 4, were organosolv-pretreated in aqueous ethanol (50% w/w ethanol) with addition of 1.10% (w/w) sulphuric acid, in a 2-L PARR® reactor chips were cooked in duplicate at 180° C. for 60 min. The liquor:wood ratio was 5:1 (w:w). After cooking, the reactor was cooled to room temperature. Solids and liquids were then separated by filtration. Solids were intensively washed with a hot ethanol solution (70° C.) followed by a tap water wash step. The moisture content of the washed pulp was reduced to about 40% with the help of a hydraulic press (alternatively a screw press can be used). The washed pulp was homogenized and stored in a fridge at 4° C. The chemical composition (hexose, pentose, lignin content) of raw chips, washed, and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydroxymethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated beetle-killed lodgepole pine chips are shown in Table 11. 120.7 g (odw) of pulp was recovered after batch organosolv processing of 400 g of wood chips (30.18% pulp yield) containing mainly fermentable into ethanol carbohydrates. Pentoses and hexoses were partially degraded resulting in 1.47 g $Kg^{-1}$ of furfural and 2.17 g $Kg^{-1}$ of 5-HMF, respectively. The lignin content in raw aspen chips and overall lignin recovery after pretreatment are shown in Table 12.

TABLE 11

Carbohydrate content of raw and pretreated beetle-killed lodgepole pine chips (BKLLP3 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 1.76 | 7.03 | 0.04 | 0.22 | 0.26 | 3.13 | 0.52 | 3.65 |
| Galactan | 2.01 | 8.05 | 0.33 | 0.61 | 0.94 | 7.57 | 4.05 | 11.62 |
| Glucan | 45.55 | 182.22 | 102.34 | 6.15 | 108.49 | 3.38 | 56.16 | 59.54 |
| Xylan | 7.22 | 28.90 | 2.34 | 0.41 | 2.75 | 1.42 | 8.10 | 9.52 |
| Mannan | 11.07 | 44.29 | 3.86 | 2.07 | 5.93 | 4.67 | 8.72 | 13.39 |
| Total: | 67.61 | 270.49 | 108.91 | 9.46 | 118.37 | | | |

TABLE 12

Lignin input in raw beetle-killed lodgepole pine chips and lignin fractions recovered after organosolv pretreatment (BKLLP3 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 106.85 | — | — |
| Self-precipitated lignin (MMW) | — | — | 0.26 |
| Precipitated lignin* (LMW) | — | — | 33.64 |
| Very low molecular wt. lignin (VLMW) | — | — | 15.33 |
| Residual lignin (HMW) | — | 9.11 | — |
| Total: | 106.85 | 9.11 | 49.23 |

*recovered from the liquor by precipitation with water; AIL - acid-insoluble lignin; ASL - acid-soluble lignin Production of ethanol from the washed pulp was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the total reaction volume was ~100 mL) and a final solids concentration of 16% (w/w). The ethanol process was run according to a SSF scheme using a commercial Trichoderma reesei fungal cellulase preparation CELLUCLAST® 1.5 L at 15 FPU $g^{-1}$ glucan supplemented with a commercial beta-glucosidase preparation (30 CBU $g^{-1}$ glucan) and an ethanologenic yeast, Saccharomyces cerevisiae strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 44.60% theoretical ethanol yield based on initial hexose input. The final ethanol beer concentration was 7.79% (w/w) (FIGS. 8a and 8b).

Example 7

Representative samples of wheat straw (*Triticum* sp.) from Eastern Washington, USA were collected. Wheat straw was cut into ~5-cm chips and stored at room temperature (moisture content at equilibrium was ~10%). The straw was organosolv-pretreated in aqueous ethanol (50% w/w ethanol) with no addition of exogenous acid or base, in a 2-L PARR® reactor. Duplicate 100-g (ODW) samples of wheat straw, designated as WS-1, were cooked in duplicate at 195° C. for 90 min. The liquor:raw material ratio was 10:1 (w/w). After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 50% with the help of a hydraulic press (alternatively a screw press can be used). The washed pulp was homogenized and stored in a fridge at 4° C. The chemical compositions (hexose, pentose, lignin content) of washed and unwashed pulps were determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated wheat straw are shown in Table 13. 46.8 g (oven-dried weight, odw) of WS-1 pulp was recovered after batch organosolv processing of 100 g of wheat straw (46.8% pulp yield) containing mainly fermentable-into-ethanol carbohydrates. Pentoses and hexoses were partially degraded resulting in 0.39 g Kg$^{-1}$ of furfural and 0.03 g Kg$^{-1}$ of 5-HMF, respectively. The lignin content in raw wheat straw and overall lignin recovery after pretreatment are shown in Table 14.

TABLE 13

Carbohydrate content of raw and pretreated wheat straw chips (WS-1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 3.85 | 3.85 | 0.00 | 0.17 | 0.17 | 4.39 | 0.00 | 4.39 |
| Galactan | 1.16 | 1.16 | 0.00 | 0.19 | 0.19 | 16.72 | 0.00 | 16.72 |
| Glucan | 54.92 | 54.92 | 35.47 | 0.00 | 35.47 | 0.00 | 64.58 | 64.58 |
| Xylan | 27.83 | 27.83 | 3.36 | 2.68 | 6.03 | 9.62 | 12.06 | 21.67 |
| Mannan | 0.53 | 0.53 | 0.00 | 0.08 | 0.08 | 15.78 | 0.00 | 15.78 |
| Total: | 88.30 | 88.30 | 38.83 | 3.12 | 41.94 | | | |

TABLE 14

Lignin input in raw wheat straw chips and lignin fractions recovered after organosolv pretreatment (WS-1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 17.44 | — | — |
| Self-precipitated lignin (MMW) | — | — | 1.7 |
| Precipitated lignin* (LMW) | — | — | 8.4 |
| Very low molecular wt. lignin (VLMW) | — | — | — |
| Residual lignin (HMW) | — | 4.31 | — |
| Total: | 17.44 | 4.31 | 10.1 |

*recovered from the liquor by precipitation with water; AIL - acid-insoluble lignin; ASL - acid-soluble lignin The potential of the produced washed wheat straw pulp for production of ethanol was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the final reaction volume was ~100 mL) and a final solids concentration of 16% (w/w). The ethanol process was run according to a SSF scheme using a commercial *Trichoderma reesei* fungal cellulase preparation CELLUCLAST® 1.5 L at 15 FPU g$^{-1}$ glucan supplemented with a commercial beta-glucosidase preparation (30 CBU g$^{-1}$ glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 88.86% theoretical ethanol yield based on initial hexose input. The final ethanol beer concentration was 6.14% (w/w) (FIGS. 9a and 9b).

Example 8

Representative samples of switchgrass (*Panicum virgatum*) from Tennessee, USA were collected. The switchgrass samples were cut to a particle size of approximately 5 cm and stored at room temperature (moisture content at equilibrium was ~10%). The switchgrass chips were organosolv-pretreated in aqueous ethanol (50% w/w ethanol) with no addition of exogenous acid or base, in a 2-L PARR® reactor. Duplicate 100-g (odw) switchgrass samples designated as SWG-1, were cooked at 195° C. for 90 min. The liquor:raw material ratio was 10:1 (w/w). After cooking, the reactor was cooled to room temperature. Solids and the spent liquor were then separated by filtration. Solids were intensively washed with a hot ethanol solution (70° C.) followed by a tap water wash step. The moisture content of the washed pulp was reduced to about 50% with the help of a hydraulic press (alternatively a screw press can be used). The washed pulp was homogenized and stored in a fridge at 4° C. The chemical composition (hexose, pentose, lignin content) of washed and unwashed pulps was determined according to a modified Klason lignin method derived from the Technical Association of Pulp and Paper Industry (TAPPI) standard method T222 om-88. Liquids were analyzed for carbohydrate degradation products (furfural, 5-hydromethylfurfural), acids, and oligo- and monosaccharides according to standard procedures established by the National Renewable Energy Laboratory. The resulting data were used to calculate overall carbohydrate and lignin recoveries and process mass balance. The carbohydrate composition and the overall carbohydrate recoveries from the raw and pretreated switchgrass are illustrated in Table 15. 45.2 g (oven-dried weight, odw) of SWG-1 pulp was recovered after batch organosolv processing of 100 g of switchgrass (45.2% pulp yield) containing mainly fermentable-into-ethanol carbohydrates. Pentoses and hexoses were partially degraded resulting in 0.917 g $Kg^{-1}$ of furfural and 0.21 g $Kg^{-1}$ of 5-HMF, respectively. The lignin content in raw switchgrass and overall lignin recovery after pretreatment are shown in Table 16.

The potential of the produced washed switchgrass pulp for production of ethanol was evaluated in 100-mL Erlenmeyer flasks. The experiments in Erlenmeyer flasks were run as follows. The pH of the washed pulp was adjusted with a water ammonia solution to pH 5.50, placed into Erlenmeyer flasks and resuspended in distilled water to a total reaction weight of 100 g (including the yeast and enzyme weight, the final reaction volume was ~100 mL) and a final solids concentration of 16% (w/w). The ethanol process was run according to a SSF scheme using a commercial *Trichoderma reesei* fungal cellulase preparation CELLUCLAST® 1.5 L at 15 FPU $g^{-1}$ glucan supplemented with a commercial beta-glucosidase preparation (30 CBU glucan) and an ethanologenic yeast, *Saccharomyces cerevisiae* strain Y-1528 at 10 g/L dry cell wt. capable of fermenting all hexoses. The mixture was incubated at 36° C., 150 rpm for 48 h. Samples were taken for ethanol analysis by gas chromatography at 0, 24, 36, and 48 h. The ethanol yield obtained was 82.51% theoretical ethanol yield based on initial hexose input. The final ethanol beer concentration was 5.97% (w/w) (FIGS. 9a and 9b).

While this invention has been described with respect to the exemplary embodiments, those skilled in these arts will understand how to modify and adapt the systems, processes and equipment configurations disclosed herein for continuously receiving and controllably commingling lignocellulosic feedstocks with counter-flowing organic solvents. Certain novel elements disclosed herein for processing a continuous incoming stream of lignocellulosic feedstocks with countercurrent flowing or alternatively, concurrent flowing organic solvents for separating the lignocellulosic materials into component parts and further processing thereof, can be modified for integration into batch systems configured for processing lignocellulosic materials. For example, the black liquors produced in batch systems may be de-lignified and then a portion of the de-lignified black liquor used to pretreat a new, fresh batch of lignocellulosic materials prior to batch organosolv cooking, while the remainder of the de-lignified black liquor is further processed into component parts as disclosed herein. Specifically, the fresh batch of lignocellulosic materials maybe controllably commingled with portions of the de-lignified black liquor for selected periods of time prior to contacting, commingling and impregnating the batch of lignocellulosic materials with suitable organic solvents. Also, it is within the scope of the present invention, to provide turbulence within a batch digestion system wherein a batch of lignocellulosic materials is cooked with organic solvents by providing pressurized flows of the organic solvents within and about the digestion vessel. It is optional to controllably remove portions of the organic solvent/black liquors

TABLE 15

Carbohydrate content of raw and pretreated switchgrass particles (SWG-1 pretreatment conditions) and overall carbohydrate recovery

| Component | Raw chips (%) | Raw Feedstock Input (g) | Pretreated Feedstock Output | | | Carbohydrates Recovery | | |
|---|---|---|---|---|---|---|---|---|
| | | | Pulp (g) | Liquor (g) | Total (g) | Soluble (%) | Insoluble (%) | Total (%) |
| Arabinan | 3.44 | 3.44 | 0.00 | 0.23 | 0.23 | 6.79 | 0.00 | 6.79 |
| Galactan | 0.93 | 0.93 | 0.00 | 0.18 | 0.18 | 19.48 | 0.00 | 19.48 |
| Glucan | 51.04 | 51.04 | 35.88 | 1.37 | 37.25 | 2.68 | 70.31 | 72.99 |
| Xylan | 26.69 | 26.69 | 5.37 | 3.01 | 8.39 | 11.29 | 20.14 | 31.43 |
| Mannan | 0.00 | 0.00 | 0.00 | 0.00 | 0.00 | 0.00 | 0.00 | 0.00 |
| Total: | 82.10 | 82.10 | 41.26 | 4.80 | 46.05 | | | |

TABLE 16

Lignin input in raw switchgrass particles and lignin fractions recovered after organosolv pretreatment (SWG-1 pretreatment conditions)

| Component | Raw Feedstock Input (g) | Pretreated Feedstock Solids Output (odw, g) | Pretreated Feedstock Liquids Output (odw, g) |
|---|---|---|---|
| Raw lignin (AIL + ASL) | 18.17 | — | — |
| Self-precipitated lignin (MMW) | — | — | 3.00 |
| Precipitated lignin* (LMW) | — | — | 10.6 |
| Very low molecular wt. lignin (VLMW) | — | — | — |
| Residual lignin (HMW) | — | 2.67 | — |
| Total: | 18.17 | 2.67 | 13.60 |

*recovered from the liquor by precipitation with water; AIL - acid-insoluble lignin; ASL - acid-soluble lignin from the digestion vessel during the cooking period and concurrently introduced fresh organic solvent and/or de-lignified black liquors thereby facilitating and expediting delignification of the lignocellulosic materials. It is also within the scope of the present invention to further process the de-lignified black liquors from the batch lignocellulosic digestion systems to separate and further process components parts exemplified by lignins, furfural, acetic acid, monosaccharides, oligosaccharides, and ethanol among others.

What is claimed is:

1. A modular system for organosolv fractionation of lignocellulosic feedstock into component parts and further processing of said component parts; the modular process comprising:
   a first processing module configured for receiving, physically processing, and physico-chemically digesting a lignocellulose feedstock with a separately supplied organic solvent thereby extracting component parts therefrom said feedstock, and separating said component parts into a cellulosic solids fraction and a first liquid fraction;
   a second processing module configured for receiving therein said cellulosic solids fraction and for separating therefrom at least ethanol, a first class of lignin derivatives, and a de-lignified first stillage;
   a third processing module configured for separating the first liquid fraction into a second class of lignin derivatives, a third class of lignin derivatives and a filtrate, and for recovering a portion of the organic solvent from the filtrate by distillation thereby producing a second stillage; and
   a fourth processing module configured for separating the second stillage into one or more of an acetic acid-containing liquid fraction, a fourth class of lignin derivatives, a sugar syrup, and a semi-solid waste material.

2. A modular system according to claim 1, additionally provided with a fifth processing module configured for anaerobic digestion and processing of the semi-solid waste material separated by the fourth processing module, into at least a collectable biogas and an liquid effluent.

3. A modular system according to claim 1, wherein the first processing module comprises a bin for receiving the lignocellulosic feedstock, a separating device, a digestion/extraction vessel, and a conveyance system for conveying the lignocellulosic feedstock from the bin to and through the separating device, and then into the digestion/extraction vessel.

4. A modular system according to claim 1, wherein the first processing module is configured to continuously receive, physically process, and physico-chemically digest a lignocellulosic feedstock thereby continuously producing the cellulosic solids fraction and the first liquid fraction.

5. A modular system according to claim 1, wherein the first processing module is configured to receive, physically process, and physico-chemically digest a batch of lignocellulosic feedstock thereby producing the cellulosic solids fraction and the first liquid fraction.

6. A modular system according to claim 1, wherein the first processing module is provided with a temperature-controllable and pressure-controllable digestion vessel configured to:
   receive therein the processed lignocellulosic feed stock at about a first end and to convey said feedstock therethrough to about a second end;
   receive therein an organic solvent at about the second end, and to flow said organic solvent therethrough to about the first end;
   discharge the cellulosic solids fraction through an outlet provided therefor approximate the second end; and
   discharge the first liquid fraction through an outlet provided therefor approximate the first end.

7. A modular system according to claim 6, wherein the temperature-controllable and pressure-controllable digestion vessel is configured to:
   receive therein the processed lignocellulosic feed stock at about a first end and to convey said feedstock therethrough to about a second end;
   receive therein an organic solvent at about the first end, and to circulate said organic solvent therethrough and thereabout;
   discharge the cellulosic solids fraction through an outlet provided therefor approximate the second end; and
   discharge the first liquid fraction through an outlet provided therefor approximate the second end.

8. A modular system according to claim 6, wherein the temperature-controllable and pressure-controllable digestion vessel is configured to:
   receive therein the processed lignocellulosic feed stock at about a first end and to convey said feedstock therethrough to about a second end;
   receive therein an organic solvent interposed the first end and second end, and to circulate said organic solvent therethrough and thereabout;
   discharge the cellulosic solids fraction through an outlet provided therefor approximate the second end; and
   discharge the first liquid fraction through an outlet provided therefor approximate the first end.

9. A modular system according to claim 1, wherein the first processing module is additionally provided with equipment configured to sequentially saturate and de-saturate the physically processed lignocellulosic feedstock prior to physico-chemically digesting said physically processed lignocellulosic feedstock.

10. A modular system according to claim 1, wherein the second processing module comprises a plurality of equipment selected and configured for controllable and manipulable communication and cooperation for:
    receiving therein the cellulosic solids fraction discharged from the first processing module;
    reducing the viscosity of the cellulosic solids fraction;
    enzymatic digestion of the reduced-viscosity cellulosic fraction thereby producing a liquid fraction comprising digestion products;
    fermentation of the liquid fraction comprising digestion products thereby producing a beer therefrom;
    distillation of the beer thereby producing a fuel-grade ethanol and a third stillage therefrom; and
    separating a first class of lignin derivatives from said third stillage.

11. A modular system according to claim 10, wherein the third stillage is recyclable for reducing the viscosity of the cellulosic solids fraction.

12. A modular system according to claim 10, wherein the second processing module is provided with a vessel for containing therein concurrent enzymatic digestion of the reduced-viscosity cellulosic solids fraction and fermentation of the liquid fraction comprising digestion products produced therefrom.

13. A modular system according to claim 2, wherein the fifth processing module is provided with a plurality of equipment configured for:
    receiving and biologically hydrolyzing therein the semi-solid waste material separated by the fourth processing module thereby producing a second liquid fraction;

receiving and biologically acidifying therein the second fraction thereby producing a biologically acidified liquid fraction;

receiving and biologically acetifying therein the biologically acidified liquid fraction thereby producing at least acetic acid; and receiving the at least acetic acid and biologically producing at least a biogas and a liquid effluent therefrom.

14. A modular system according to claim 13, wherein the anaerobic digestion module is additionally configured for controllably receiving and commingling a portion of said sugar syrup separated in the fourth processing module with the a third liquid fraction.

15. A modular system according to claim 2, additionally provided with a sixth processing module configured for receiving, fermenting and distilling therein said sugar syrup, and for separating therefrom a distillate and a fourth stillage.

16. A modular system according to claim 15, wherein said distillate comprises at least 1,3 propanediol.

17. A modular system according to claim 15, wherein said distillate comprises at least lactic acid.

18. A modular system according to claim 10, wherein a portion of the sugar syrup separated in the fourth processing module is controllably delivered into the second module for production therein of ethanol therefrom.

19. A modular system according to claim 1, wherein the ethanol is a fuel-grade ethanol.

\* \* \* \* \*